US010603451B2

(12) United States Patent
Reinecke et al.

(10) Patent No.: US 10,603,451 B2
(45) Date of Patent: Mar. 31, 2020

(54) CONTAINER FOR AN INHALER

(71) Applicant: Boehringer Ingelheim Vetmedica GmbH, Ingelheim am Rhein (DE)

(72) Inventors: Holger Reinecke, Emmendingen (DE); Benjamin Franzmann, Ingelheim am Rhein (DE); Marcus Rainer Rahmel, Ingelheim am Rhein (DE); Michael Aven, Ingelheim am Rhein (DE); Stefen Schuy, Ingelheim am Rhein (DE); Andree Jung, Ingelheim am Rhein (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 209 days.

(21) Appl. No.: 15/528,260

(22) PCT Filed: Nov. 19, 2015

(86) PCT No.: PCT/EP2015/002314
§ 371 (c)(1),
(2) Date: May 19, 2017

(87) PCT Pub. No.: WO2016/078763
PCT Pub. Date: May 26, 2016

(65) Prior Publication Data
US 2017/0368274 A1     Dec. 28, 2017

(30) Foreign Application Priority Data

Nov. 20, 2014   (EP) ..................................... 14003898
Mar. 27, 2015   (EP) ..................................... 15000904

(51) Int. Cl.
*A61M 15/00*     (2006.01)
*A61M 15/08*     (2006.01)
(Continued)

(52) U.S. Cl.
CPC ............. *A61M 15/009* (2013.01); *A61D 7/04* (2013.01); *A61M 11/006* (2014.02);
(Continued)

(58) Field of Classification Search
CPC ............ A61M 15/009; A61M 15/0091; A61M 15/08; A61M 11/006; A61M 11/008
See application file for complete search history.

(56) References Cited

U.S. PATENT DOCUMENTS 3,255,972 A    6/1966   Hultgren et al.
4,008,830 A    2/1977   Meshberg
(Continued)

FOREIGN PATENT DOCUMENTS

EP     0 182 094 A2    5/1986
EP     0 653 359 A1    5/1995
(Continued)

*Primary Examiner* — Nathan R Price
*Assistant Examiner* — Anh Bui
(74) *Attorney, Agent, or Firm* — David S. Safran; Roberts Calderon Safran & Cole, P.C.

(57) ABSTRACT

A container for holding, dispensing and/or storing a preferably liquid medicament preparation is proposed, which comprises an inner space for the medicament preparation and an at least partially multi-layered wall structure defining the inner space, the wall structure comprising a first layer with a first through-opening of less than 40 μm. Alternatively or additionally, the wall structure comprises a second and third layer, a second through-opening being provided in the second layer and the third layer covering or closing off the wall structure.

19 Claims, 8 Drawing Sheets

(51) Int. Cl.
  *A61M 11/02* (2006.01)
  *A61D 7/04* (2006.01)
  *B05B 11/00* (2006.01)
  *A61M 11/00* (2006.01)
  *A61M 16/00* (2006.01)

(52) U.S. Cl.
  CPC ........... *A61M 11/008* (2014.02); *A61M 11/02* (2013.01); *A61M 15/0015* (2014.02); *A61M 15/0035* (2014.02); *A61M 15/0038* (2014.02); *A61M 15/0086* (2013.01); *A61M 15/0091* (2013.01); *A61M 15/08* (2013.01); *B05B 11/0054* (2013.01); *B05B 11/00412* (2018.08); *B05B 11/00442* (2018.08); *B05B 11/00446* (2018.08); *A61M 2016/0024* (2013.01); *A61M 2205/8281* (2013.01); *A61M 2207/00* (2013.01); *A61M 2250/00* (2013.01); *B05B 11/0039* (2018.08)

(56) References Cited

U.S. PATENT DOCUMENTS

| | | | |
|---|---|---|---|
| 4,546,790 A | 10/1985 | Huber et al. | |
| 5,242,085 A | 9/1993 | Richter et al. | |
| 5,242,086 A * | 9/1993 | Richter | B65D 1/0215 222/105 |
| 5,275,311 A | 1/1994 | Piarrat | |
| 5,301,838 A | 4/1994 | Schmidt et al. | |
| 5,337,740 A | 8/1994 | Armstrong et al. | |
| 5,513,761 A | 5/1996 | Kobayashi et al. | |
| 5,562,219 A | 10/1996 | de Pous et al. | |
| 5,772,080 A | 6/1998 | de Pous et al. | |
| 5,799,809 A | 9/1998 | Sako | |
| 5,833,088 A | 11/1998 | Kladders et al. | |
| 5,884,759 A | 3/1999 | Gueret | |
| 6,145,703 A | 11/2000 | Opperman | |
| 6,223,933 B1 * | 5/2001 | Hochrainer | B65D 83/0055 220/723 |
| 6,244,472 B1 | 6/2001 | Hennemann | |
| 6,266,943 B1 | 7/2001 | Nomoto et al. | |
| 6,276,558 B1 | 8/2001 | Kneer | |
| 6,312,641 B1 | 11/2001 | Hutchinson | |
| 6,402,055 B1 | 6/2002 | Jaeger et al. | |
| 6,425,571 B1 | 7/2002 | Schadewald et al. | |
| 6,491,897 B1 | 12/2002 | Freund et al. | |
| 6,685,691 B1 | 2/2004 | Freund et al. | |
| 6,916,011 B2 | 7/2005 | Kitazawa et al. | |
| 6,988,496 B1 * | 1/2006 | Eicher | A61M 15/0065 128/200.14 |
| 7,451,884 B2 | 11/2008 | Kuehn et al. | |
| 7,470,422 B2 | 12/2008 | Freund et al. | |
| 7,571,722 B2 | 8/2009 | Wuttke et al. | |
| 7,802,568 B2 | 9/2010 | Eicher et al. | |
| 9,084,660 B2 | 7/2015 | Karle et al. | |
| 2004/0013513 A1 | 1/2004 | Jeswani et al. | |
| 2006/0016449 A1 | 1/2006 | Eicher et al. | |
| 2012/0103326 A1 | 5/2012 | Karle et al. | |

FOREIGN PATENT DOCUMENTS

| | | |
|---|---|---|
| WO | 2005/007999 A1 | 1/2005 |
| WO | 2005/079997 A1 | 9/2005 |

* cited by examiner

CONTAINER FOR AN INHALER

BACKGROUND OF THE INVENTION

Field of the Invention

The present invention relates to a container for holding, dispensing and/or storing a preferably fluid medicament preparation, particularly for an inhaler, as well as an inhaler, preferably for insertion into a nostril, particularly of a horse, and a method for producing a container.

Description of Related Art

The present invention relates in particular to a so-called Soft Mist Inhaler (SMI), i.e., an inhaler which produces a spray mist (aerosol) that spreads out only relatively slowly. Inhalers of this kind in the sense of the present invention are, in particular, inhalers in which an aerosol is dispensed at a speed of less than 2 m/s, preferably about 1.6 m/s or less and most particularly preferably less than 1 m/s, (measured in each case at a distance of 10 cm from a discharge nozzle) and/or wherein the dispensing or nebulization of a dose—of preferably 10 to 50 μl of a medicament preparation—takes longer than 0.7 s, particularly about 1 s or longer.

International Patent Application Publication WO 2005/079997 A1 and corresponding U.S. Pat. No. 7,571,722 disclose an inhaler, which constitutes an SMI in the sense of the present invention. The known inhaler comprises, as reservoir for a medicament preparation that is to be nebulized, an insertable rigid container with an inner pouch containing the medicament preparation and a pressure generator having a drive spring for conveying and nebulizing the medicament preparation. Nebulization is carried out without the use of propellant gas, namely by the force of the drive spring.

The known SMI operates with a container for holding, dispensing and/or storing a preferably liquid medicament preparation. The container comprises a dispensing region for dispensing a medicinal liquid and an opening in the base region for ventilation, the opening in the base region being covered by a film, which is pierced in order to use the inhaler.

It has been found that volatile substances can escape to a significant degree through the ventilation hole provided in the base, and this limits shelf life and/or in use stability depending on the particular filling. The consequent reduction in shelf life and/or in use stability is exacerbated particularly in inhalers for large animals by the fact that inhalers of this kind are regularly used in different regions with varying temperatures.

US Patent Publication 2006/0016449 A1 discloses a cartridge for a liquid with a stiff casing which has an opening at the bottom. Additionally, an insert is provided at the bottom of the casing which includes an opening in the form of a micro-opening which communicates with the opening in the bottom of the stiff casing. The outside of the casing bottom can be provided with a sealing foil which covers the opening in the bottom or in the insert in the bottom.

SUMMARY OF THE INVENTION

The problem solved by the present invention is to provide a container, an inhaler and a method by which shelf life and/or in use stability can be improved, particularly under difficult or fluctuating environmental conditions.

The above problem is solved by a container, an inhaler and a method as described herein.

The proposed container for holding, dispensing and/or storing a preferably liquid medicament preparation comprises an inner space for the medicament preparation, particularly for holding it. Moreover, the proposed container comprises an at least partially multi-layered wall structure defining the inner space. The multi-layered wall structure is provided particularly in the base region of the container. Also, the wall structure of the proposed container comprises a first layer in which a first through-opening is provided.

In a first aspect of the present invention it is provided that the first through-opening has an, in particular hydraulic, diameter of less than 40 μm. Alternatively or additionally, the wall structure additionally comprises a second layer and a third layer, while in the second layer there is a second through-opening different from the first through-opening and the third layer covers or closes off the wall structure.

It has proved particularly advantageous to modify the venting structure of the container such that the diffusion of volatile substances is reduced and at the same time ventilation is still possible. The present invention in this respect overcomes the prejudice that any reduction in the cross-section of a venting hole has only an insignificant effect on the exchange between the inner space and the environment of a container. In fact, it has been found surprisingly that in principle this is the case with the diameters that have hitherto been conventional, but not with a diameter of less than 40 μm.

Moreover, it has proved particularly advantageous to arrange a plurality of through-openings, particularly behind one another. This, too, surprisingly improves the shelf life and/or in use stability of a medicament preparation that may be placed in the container, particularly by reducing the escape of volatile constituents.

One combination which has proved particularly advantageous is the one in which a plurality of layers with through-openings are arranged behind one another, at least one of the through-openings having a diameter of less than 40 μm. In this way it has proved possible to reduce the escape of volatile constituents to such an extent that, depending on the formulation used, the shelf life and/or in use stability of a medicament preparation which may be arranged in the proposed container can be improved by a multiple, compared with known systems, particularly depending on the solvents used.

It is preferable if the first through-opening and the second through-opening are fluidically connected to one another and/or to the inner space of the container. This ensures that the through-openings can function as ventilation openings.

It is preferable if the second through-opening is not in direct contact with the first through-opening, the through-openings are spatially separated from one another, spaced apart and/or arranged independently of one another or formed in different parts.

It is also preferable if the first through-opening is of tube-shaped formation. This geometry has additionally proved advantageous for reducing the escape of volatile constituents.

Most particularly preferably, the first through-opening, particularly if it has a (hydraulic) diameter of less than 40 μm, is produced by laser drilling. By laser drilling, a through-opening with very small diameters, in particular, can be produced with extraordinary precision, thus guaranteeing reliable ventilation.

Particularly preferably, the first through-opening is the only through-opening of the first layer. Theoretically it is certainly possible for the first layer also to have a plurality of through-openings of correspondingly small diameter of preferably less than 40 μm. However, particularly good results have been obtained with only one through-opening.

It is also particularly preferable if the (hydraulic) diameter of the first through-opening is less than 40 μm, preferably less than 30 μm, particularly at least substantially or less than 25 μm. It is true that significantly improved shelf life and/or in use stability has been achieved with (hydraulic) diameters of less than 50 μm, but the optimum is between 15 and 40 μm, particularly between 20 and 30 μm. Within this range the shelf life and/or in use stability can be improved particularly markedly while at the same time still ensuring adequate ventilation.

The first layer with the first through-opening is preferably at least substantially flat, film-like, plate-like, metallic and/or at least substantially round. A thin configuration of the first layer is particularly conducive to precise and reliable manufacture of through-openings with correspondingly small diameters. Metallic films have proved particularly reliable in this context, as, with the small (hydraulic) diameters envisaged, the chemical and mechanical stability of metal, particularly aluminum, contributes to the reliability of the container as a whole.

The first layer preferably covers the (inner) base of the container, a wall or sleeve forming the container, at least substantially completely. A first layer which is at least substantially round and/or which covers the base completely has proved advantageous for leak-tight or sealing attachment to the container wall.

It is preferable if the first layer has an, in particular central, convexity or indentation in which the first through-opening is arranged. This makes it possible to achieve a leak-tight attachment to or formation with the wall of the container in an edge region and at the same time to allow a safety gap between the first through-opening and adjacent layers or elements, so that blockage or other adverse effects on the first through-opening can be effectively prevented. In particular, it is provided that the first layer has a convexity facing towards the inner space of the container and/or an indentation/cavity on a side remote from the inner space of the container.

It is also preferable if the second layer also comprises a convexity or indentation. The indentation of the second layer preferably forms a cavity between the second and third layers.

The third layer is particularly a cover, particularly a sealing film or cover film. Preferably, the third layer is pierced, particularly punctured, to enable the medicament preparation to be removed. The cavity preferably arranged behind the third layer makes it possible to carry out the piercing without affecting the first or second layer. In a variant the first layer may also be adjacent to the third layer and the convexity or indentation of the first layer may correspondingly permit piercing without any risk of deterioration or damage to the first layer. However, it is particularly preferable to arrange the first layer on the side of the second layer remote from the third layer, as in this way the first layer can be protected by the second layer in the event of destruction, piercing or perforation of the third layer.

It is particularly preferable if the convexity or indentation of the first and second layers correspond to one another, particularly so that the convexities or indentations are superimposed, without the layers touching in the immediate vicinity of the respective through-opening. This has proved particularly advantageous for preventing adverse effects on the first through-opening, in particular.

The first layer may comprise other layers, particularly ones that correspond or are similar in terms of their finish or structure and/or ones that also comprise the first through-opening and/or the convexity or indentation, particularly one or more coats of paint, passivation layers, adhesive layers, sealing layers or the like, so that a composite film can be formed. The first layer may be part of a composite film or may preferably at least substantially form at least 80% or 90% of such a film, based on its weight or volume.

According to another aspect of the present invention the first layer is materially and/or sealingly and/or directly connected to the second layer. This advantageously enables a fluidic connection between the inner space of the container and the environment to be obtained exclusively through the first and second through-opening, particularly without any possibility of the first and/or second through-opening being circumvented, for example by a bypass.

It has proved advantageous, in conjunction with the connection of the first layer to the second layer, for the connection to be in an annular portion around the first or through the second through-opening. Particularly preferably, the first layer and the second layer are sealingly glued, sealed or otherwise materially connected to one another in an annular configuration around the first or second through-opening. This allows for a leak-tight attachment while at the same time reducing the risk of damage to the first and/or second through-opening.

According to another aspect of the present invention it is provided that the first through-opening and the second through-opening are arranged (fluidically) behind one another. This makes it possible to produce a double barrier which positively influences shelf life and/or in use stability. It is also preferable if the first through-opening and the second through-opening are arranged at least substantially in alignment with one another. This makes assembly easier and prevents the flow resistance for ventilating the inner space of the container from increasing in an unintended manner in an interstice formed between the first and second through-openings. The first layer and the second layer are preferably arranged at least substantially parallel to one another.

In another aspect of the present invention a spacing is provided between the first layer and the second layer in the region of the first through-opening and/or the second through-opening, the spacing preferably being greater than 20 μm, preferably greater than 50 μm, particularly greater than 100 μm or 200 μm and/or less than 3 mm, preferably less than 2 mm, particularly less than 1 mm. In this way the first through-opening can be protected from contamination or a change in cross-section resulting from contact with other parts, particularly during assembly. Moreover, a corresponding spacing has proved advantageous for reducing the escape of volatile constituents of the medicament preparation from the container.

The second layer is preferably formed in one piece with the base and/or a side wall of the container. The container is particularly deep drawn or otherwise formed as a continuous piece, particularly made of metal, for example aluminum. The second through-opening is therefore preferably arranged in the wall or sleeve that directly forms the container and this wall or sleeve that directly forms the container forms or comprises the second layer.

Alternatively or additionally, however, the first layer may also be formed in one piece with the base and/or the side wall of the container. It is thus possible in principle for the first through-opening with an, in particular hydraulic, diameter of less than 40 μm to be provided in the wall or sleeve that directly forms the container. However, it has proved particularly advantageous to provide the first through-opening having the diameter of less than 40 µm in a layer that is separate from the wall or sleeve directly forming the container, said layer being materially connected to the wall or sleeve that directly forms the container.

The second through-opening preferably comprises, in particular, a hydraulic, diameter which is greater than the, in particular hydraulic, diameter of the first through-opening. The, in particular hydraulic, diameter of the second through-opening is preferably greater than 50 µm, particularly greater than 100 µm or 150 µm. Advantageously, a corresponding diameter can be produced more easily in the wall or sleeve that directly forms the container.

In one aspect of the present invention, it is provided that the third layer is configured as a sealing film. Alternatively or additionally, the third layer is embodied and arranged to cover or close off the first through-opening and/or the second through-opening on a side of the first through-opening and/or second through-opening remote from the inner space of the container. In particular, it is thus provided that the first through-opening and the second through-opening are arranged fluidically behind one another and externally covered or sealed off in airtight manner by the third layer, particularly as a sealing film.

It is also preferable if the third layer is fluidically connected to the inner space by means of the first through-opening and the second through-opening. It is thus particularly envisaged that a continuous fluidic connection is formed between the inner space of the container and an inner side of the third layer, particularly sealing film, through the first through-opening and through the second through-opening.

It is also preferably envisaged that the first layer is arranged or provided inside the container or the wall or sleeve directly forming the container, particularly preferably on the bottom and/or as an inlay. This has also proved advantageous in terms of simple and reliable assembly.

Alternatively or additionally, it is provided that the second layer and/or the third layer is arranged on the side of the first layer remote from the inner space.

The first layer is preferably arranged inside the container. The third layer is preferably arranged outside the container. This advantageously produces a series of layers from the inside outwards, starting with the first layer comprising the first through-opening, followed by the second layer comprising the second through-opening which preferably forms the direct container wall, and followed by the external third layer, which is preferably embodied as a sealing film.

The third layer or sealing film may be removable or pierceable or in some other way modifiable so as to allow the inner space to be fluidically connected to the environment of the container through the first and/or second through-opening.

According to another aspect of the present invention, it is provided that between the second layer and the first layer and/or between the second layer and the third layer in the region of the first through-opening and/or second through-opening, a cavity is formed, particularly produced by thermoforming and/or deep drawing, the volume of the cavity preferably being greater than 0.2 µl, preferably greater than 0.5 µl, particularly greater than 1 µl and/or less than 10 µl, preferably less than 6 µl, particularly less than 4 µl. In this way, the first and/or second through-opening can advantageously be protected, particularly even when the third or sealing layer is pierced or otherwise removed.

Another aspect of the present invention which may also be implemented independently relates to an inhaler with a container according to one of the aspects described hereinbefore, the inhaler comprising the container and/or being configured to accommodate the container, and the inhaler being configured to cut through or remove the third layer without affecting the first layer.

Another aspect of the present invention which may also be implemented independently relates to a method for producing a proposed container, wherein an inlay is inserted as the first layer into a container blank or a sleeve comprising a wall, particularly a container wall directly forming the container, the inlay having a first through-opening which preferably has a (hydraulic) diameter of less than 40 µm, and wherein, in a region surrounding the opening, the inlay is sealingly connected to the wall of the container blank or the sleeve, preferably by heat-sealing.

It is preferable if the first through-opening is introduced into the first layer by laser drilling, particularly after the first layer has been thermoformed and/or deep drawn in the region of the first through-opening and/or before the first layer is placed as an inlay in the container blank or the sleeve. This allows easy manufacture and assembly which is not very prone to error and is consequently associated with good yields. The first through-opening may alternatively also be produced after the fitting of the first layer, particularly within the sleeve.

A container wall which directly forms the container or the sleeve in the sense of the present invention is in particular a wall which predominantly or at least substantially delimits the inner space of the container, particularly on at least two, three, four or five sides and/or delimits it both laterally and in the direction of the base.

The container blank or the sleeve in the sense of the present invention is particularly a cup-like and/or at least substantially cylindrical element with a base region and a side wall adjacent to the base region, which are preferably metallic, formed from aluminum and/or formed in one piece, particularly by thermoforming and/or deep drawing. However, other solutions are also possible.

A through-opening in the sense of the present invention is preferably an orifice, a breach in the wall or some other connection between a preferably first and second flat side of the layer in question, thus producing a fluidic connection, particularly a connection which allows the exchange of air or substances.

A hydraulic diameter in the sense of the present invention is, in particular, a diameter of a tube or an opening, particularly a through-opening, having a circular cross-section, with a diameter, or an opening or through-opening, with a geometry which produces the same pressure loss as an opening or through-opening of circular cross-section at the same flow volume or the same flow velocity.

A layer in the sense of the present invention is preferably a flat structure. A layer preferably has a maximum thickness of material which exceeds its extent more than four times, preferably more than eight times, particularly more than ten times. A layer in the sense of the present invention is particularly thin, flat, film-like, sheet-like or similar. A layer in the sense of the present invention preferably also has a material thickness which is less than 1 mm, preferably less than 0.5 mm, particularly less than 0.3 mm or 0.25 mm. A layer in the sense of the present invention preferably also has a surface extent which is greater than 0.5 cm, particularly greater than 1 cm and/or amounts to more than 20 times, preferably more than 50 times, particularly, more than 100 times the (average) thickness of material. A layer in the sense of the present invention is preferably free from material transitions, is homogeneous, and/or comprises only, exclusively or exactly one material, particularly metal.

A further aspect of the present invention, which can also be implemented independently, relates to a medical use of the container and/or the inhaler, in particular as described above.

In a further aspect, the present invention concerns the container and/or the inhaler for the use (in a method) for the management/treatment of airway disease in equines, preferably horses, preferably the airway disease is a pulmonary disease, more preferably the airway disease is selected from the group consisting of: recurrent airway obstruction (RAO), summer pasture associated obstructive pulmonary disease (SPAOPD), and inflammatory airway disease (IAD).

The invention further concerns a method of treating an airway disease comprising administering a therapeutic effective amount of an active substance or a pharmaceutically acceptable salt thereof using said container and/or inhaler to a patient, preferably an equine patient, more preferably a horse, in need thereof. Preferably the airway disease is a pulmonary disease, more preferably the airway disease is selected from the group consisting of: recurrent airway obstruction (RAO), summer pasture associated obstructive pulmonary disease (SPAOPD), and inflammatory airway disease (IAD).

The term "equine" means of or belonging to the family Equidae, which includes the horses, asses, and zebras, preferably horses. In addition, the term "equine" encompasses also hybrids of members of the family Equidae (e.g. mules, hinnies, etc.)

The term "patient" or "subject" embraces mammals, such as primates including humans. The term "patient" or "subject" as used herein relates specifically to horses, especially horses suffering from airway disease (particularly pulmonary disease), preferably from recurrent airway obstruction (RAO) also called heaves or equine COPD and/or summer pasture associated obstructive pulmonary disease (SPAOPD) also called Summer Pasture Associated Recurrent Airway Obstruction (SPARAO) and/or inflammatory airway disease (IAD), most preferably from RAO.

The term "airway disease" in horses means the following: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, chronic interstitial lung disease and upper respiratory tract functional disorders.

The term "pulmonary disease" means: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, chronic interstitial lung disease.

The term "recurrent airway obstruction (RAO)" in horses means the following: a chronic syndrome of mature horses with reversible airway obstruction in the stable showing periods of labored breathing at rest during exacerbation.

The term "Summer Pasture Associated Obstructive Pulmonary disease (SPAOPD)" in horses means the following: a chronic syndrome, which shares many clinical and pathological similarities with RAO at rest on the pasture, suggesting similar pathogenesis, however, it is caused by different antigens.

The term "inflammatory airway disease (IAD)" in horses means the following: a chronic syndrome of horses showing poor performance or coughing or excess tracheal mucus without showing periods of laboured breathing at rest.

The term "effective amount" as used herein means an amount sufficient to achieve a reduction of airway disease in a horse when ciclesonide is administered at a dosage as described herein. The progress of the therapy (improvement of airway disease, particularly pulmonary disease, preferably recurrent airway obstruction (RAO) and/or Summer Pasture Associated Obstructive Pulmonary disease (SPAOPD) and/or inflammatory airway disease (IAD), most preferably RAO as described herein) can be monitored by standard airway/pulmonary diagnosis, for example, by clinical examination, airway fluid cytology, endoscopy, lung function measurement, or blood-gas analysis.

The term "pharmaceutically acceptable derivative thereof" means, but is not limited to, pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

In a preferred aspect of the present invention, the active substance administered using the container and/or inhaler of the present invention is a glucocorticoid, preferably ciclesonide and/or budesonide and/or fluticasone, most preferably ciclesonide.

The term "glucocorticoid" refers to a class of steroid hormones that bind to the glucocorticoid receptor (GR), which is present in almost every vertebrate animal cell. The name glucocorticoid (glucose+cortex+steroid) derives from its role in the regulation of the metabolism of glucose, its synthesis in the adrenal cortex, and its steroidal structure.

Glucocorticoids are part of the feedback mechanism in the immune system that turns immune activity (inflammation) down. They are therefore used in medicine to treat diseases caused by an overactive immune system, such as allergies, asthma, autoimmune diseases, and sepsis.

Preferred glucocorticoids according to the present invention are ciclesonide and/or budesonide and/or fluticasone.

A "ciclesonide" ((11β,16α)-16,17-[[(R)-Cyclohexylmethylene]bis(oxy)]-11-hydroxy-21-(2-methyl-1-oxopropoxy)pregna-1,4-diene-3,20-dione, $C_{32}H_{44}O_7$, Mr=540.7 g/mol) is well known in the art and means/describes a glucocorticoid used to treat asthma and allergic rhinitis in humans. It is marketed for application in humans under the brand name Alvesco™ for asthma and Omnaris™/Omniair™ for hay fever in the US and Canada. Ciclesonide is a prodrug. It is transformed into the active metabolite C21-C21-desisobutyrylciclesonide (=desciclesonide) via hydrolysis by intracellular esterases in the lung. Ciclesonide is a non-halogenated glucocorticoid, which predominantly exists in its form as R-Enantiomer.

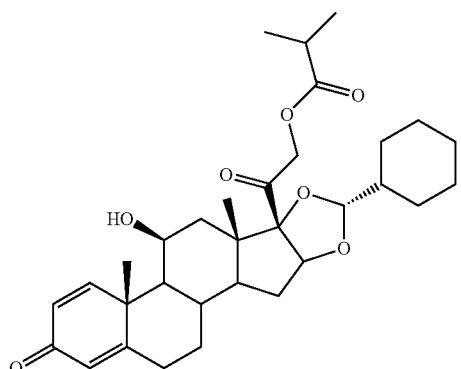

Ciclesonid

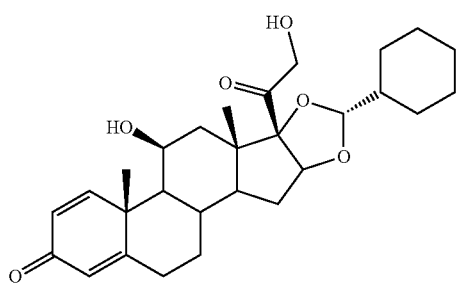

Desciclesonid

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e., an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound (also called the active metabolite), for example, by hydrolysis in blood or by activation via oxidation as in case of thioether groups. Most common prodrugs include esters and amide analogues of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can usually be readily prepared from the parent compounds using methods known in the art.

In another preferred aspect of the present invention the active substance administered using the container and/or inhaler of the present invention is a muscarinic antagonist, preferably LAMA1.

The term "muscarinic antagonists" refers to a group of substances that block the effects of acetylcholine on muscarinic receptors to reverse airway obstruction [Barnes, 2004]. Therefore "muscarinic antagonists" are also often denoted as "anticholinergics" or "anticholinergic agents".

Examples for muscarinic antagonists include ipratropium bromide (which is often administered in equine medicine), atropine, aclidinium bromide, umeclidinium and glycopyrrolate.

The following subgroups of muscarinic antagonists can be defined:
1. long-acting muscarinic antagonists" or "LAMAs";
2. short-acting muscarinic antagonists" or "SAMAs".

An example of a LAMA is glycopyrrolate. An example of a SAMA is atropine.

The term "long-acting muscarinic antagonists" or "LAMAs" refers to a group of substances that block the effects of acetylcholine on muscarinic receptors for a longer period of time. Examples for LAMAs include tiotropium bromide or anticholinergics of the following general formula I:

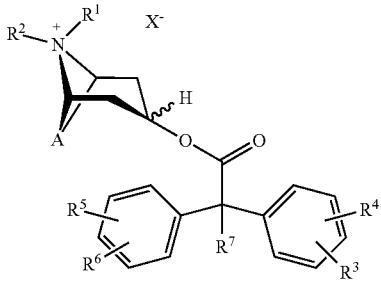

wherein
A denotes a double-bonded group selected from among

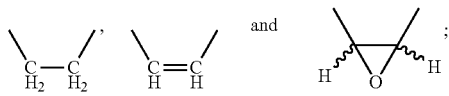

X— denotes an anion with a single negative charge,
R1 and R2 denote C1-C4-alkyl, which may optionally be substituted by hydroxy or halogen;
R3, R4, R5 and R6, which may be identical or different, denote hydrogen, C1-C4-alkyl, C1-C4-alkyloxy, hydroxy, CF3, CN, NO2 or halogen;
R7 denotes hydrogen, C1-C4-alkyl, C1-C4-alkyloxy, C1-C4-alkylene-halogen, halogen-C1-C4-alkyloxy, C1-C4-alkylene-OH, CF3, —C1-C4-alkylene-C1-C4-alkyloxy, —O—COC1-C4-alkyl, —O—COC1-C4-alkyl-halogen, —O—COCF3 or halogen,
optionally in the form of the individual optical isomers, mixtures of the individual enantiomers or racemates thereof, while if A denotes

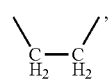

R1 and R2 denote methyl and
R3, R4, R5 and R6 denote hydrogen,
R7 cannot also be hydrogen.

Anticholinergics of the general formula I and processes for preparing them are disclosed for example in WO02/32899, which is hereby incorporated therein.

The term "LAMA 1" describes a novel anticholinergic agent with the chemical name (1a,2b,4b,5a,7b)-3-Oxa-9-azoniatricyclo [3.3.1.02,4]nonane, 9,9-dimethyl-7-(1-oxo-2,2-diphenylpropoxy)-bromide or alternatively (short name) scopine 2,2-diphenylpropionate methobromide.

LAMA 1 (=scopine 2,2-diphenylpropionate methobromide) has the following chemical structure:

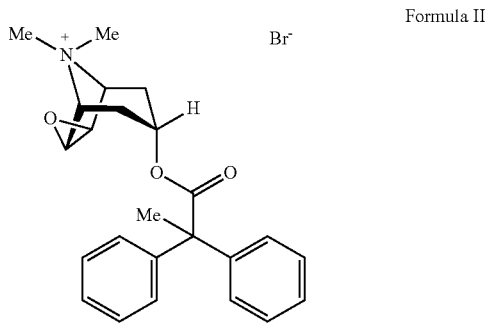

Formula II

LAMA 1 has the sum formula C24H28NO3*Br and has a molecular weight of 458.39 g/mol.

*In a further aspect of the present invention the active substance administered using the container or inhaler of the present invention is a beta-2 adrenoreceptor agonists.

The term "beta-2 adrenoreceptor agonists" or "beta-2 adrenergic agonists" refers to a group of substances that stimulate α2-adrenergic receptors to relax airway smooth muscles [Tashkin and Fabbri, 2010].

The following subgroups of "beta-2 adrenoreceptor agonists" or "beta-2 adrenergic agonists" can be defined:
1. "long-acting beta-2 adrenergic agonists" or "LABAs";
2. "short-acting beta-2 adrenergic agonists" or "SABAs".

The term "long-acting beta-2 adrenergic agonists" or "LABAs" refers to a subgroup of substances that stimulate β2-adrenergic receptors to relax airway smooth muscles for a longer period of time.

Examples for LABAs include salmeterol, formoterol, bambuterol, indacaterol, vilanterol, abediterol and olodaterol hydrochloride.

Examples for beta-2 adrenoreceptor agonists of the SABA type include salbutamol or albuterol, clenbuterol, pirbuterol and fenoterol.

In a further aspect of the present invention, the active substance administered using the container and/or inhaler of the present invention is a combination of any of the above mentioned active substances, preferably a combination of a glucocorticoid and a muscarinic antagonists, more preferably ciclesonide and LAMA-1.

The medicament preparation according to the present invention preferably comprises the active substance or a pharmaceutically acceptable salt thereof. The medicament preparation preferably is a fluid or liquid, in particular comprising the active substance or the pharmaceutically acceptable salt thereof. The medicament preparation preferably comprises one or more solvents, in particular water, alcohol, ethanol or the like. The medicament preparation in particular is a solution and/or suspension from the active substance or a pharmaceutically acceptable salt thereof, in particular an aquenous, alcoholic, and/or ethanolic solution and/or suspension.

In a further aspect of the present invention, which can also be realized independently, a medicament preparation is stored within the container according to the present invention, the medicament preparation comprising the active substance or a pharmaceutically acceptable salt thereof and/or a solvent such as alcohol, water or a blend thereof. It has been surprisingly shown that storing the medical preparation, the active substance, the salt and/or the solvent is/are particularly efficient and effective, in particular improving stability or possible storing time.

The stability preferably is a chemical stability of the active substance or the pharmaceutically acceptable salt thereof and/or of the concentration of the active substance within the medicament preparation and/or the stability of the amount or concentration of the, preferably volatile, solvent of the medicament preparation.

Preferably, the container can be opened for pressure compensation. It has been found particularly advantageous that the stability of the pharmaceutical preparation, the active substance and/or the pharmaceutically acceptable salt thereof can be increased resulting from the combination of the medicament preparation, the active substance, in particular being or comprising ciclesonide and/or budesonide and/or fluticasone, the medicament preparation preferably being a liquid comprising the active substance and a solvent, like alcohol, preferably ethanol, and the container storing it, even if the container has already been opened for pressure compensation.

The aspects and features mentioned above may be implemented independently of one another, but also in any desired combinations.

Further advantages, features, properties and aspects of the present invention will be apparent from the following description with reference to the accompany drawings.

DETAILED DESCRIPTION OF THE INVENTION

Figure 1:
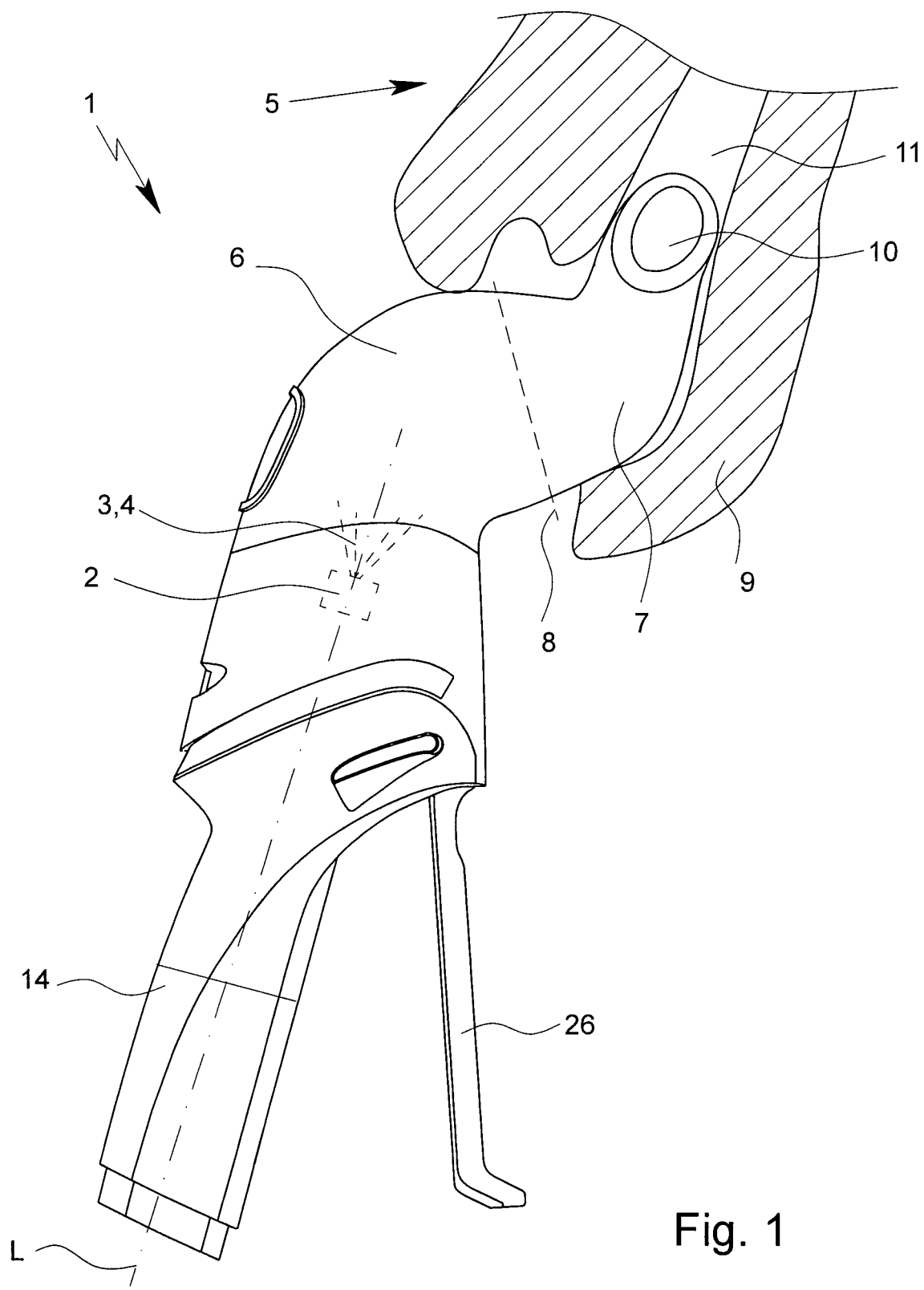
FIG. 1 is a side view of a proposed inhaler.

In the figures, the same reference numerals are used for the same or similar parts, and corresponding or comparable properties and advantages may be achieved even though the relevant description has not been repeated.

Figure 2:
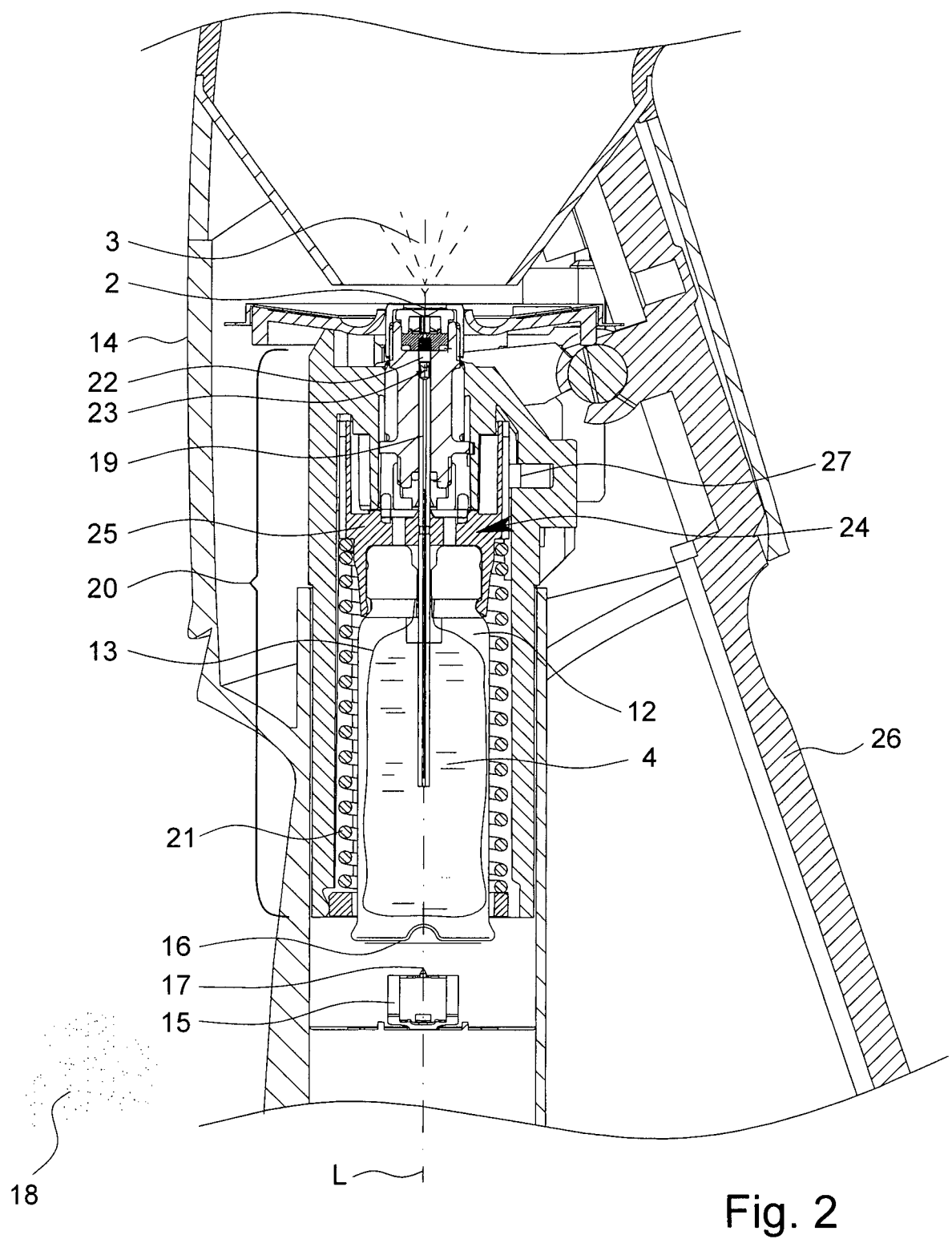
FIG. 2 is a detail of the proposed inhaler in the region of the relaxed pressure generator.
Figure 3:
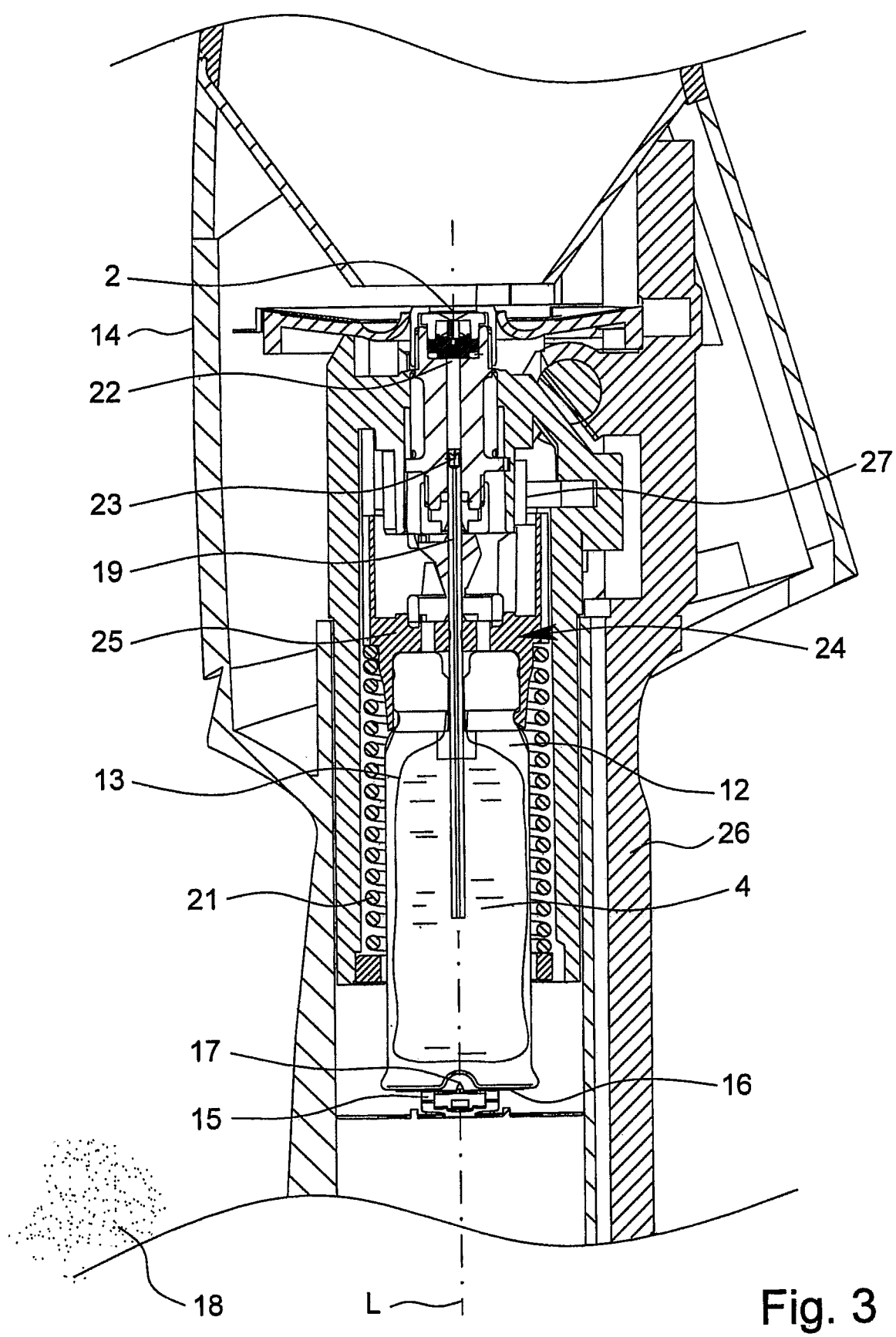
FIG. 3 is a detail of the proposed inhaler in the region of the tensioned pressure generator.

First of all, the backgrounds and the particularly preferred field of use of the present invention are explained in more detail hereinafter with reference to FIGS. 1 to 3.

FIG. 1 shows a view of a proposed inhaler 1. The inhaler 1 comprises a discharge nozzle 2 indicated by dashed lines in FIG. 1 which is preferably configured to form an aerosol 3 with a medicament preparation 4.

When the medicament preparation 4, preferably a liquid, is nebulized, the preferably respirable aerosol 3 is formed, which can be breathed in or inhaled by a user or patient (not shown), such as an animal, a human or preferably a large animal, particularly a horse 5. Usually, inhalation takes place at least once a day, more particularly several times a day, preferably at predetermined time intervals, particularly depending on the disease.

The inhaler 1 preferably has a chamber 6 or dispensing device 7 for fluidically connecting the chamber 6 to a body orifice, preferably a nostril 9, particularly that of a horse 5. The dispensing device 7 is preferably formed in one piece with the chamber 6 or connected thereto. The aerosol 3 may be temporarily stored in a chamber 6 and/or dispensed by the dispensing device 7.

The user or patient, particularly the horse 5, can inhale the aerosol 3, while air can preferably be sucked in through the chamber 6.

The chamber 6 is preferably embodied to hold and/or temporarily store the aerosol 3 produced by the inhaler 1. The chamber 6 is preferably arranged, or adapted to be arranged, downstream of the discharge nozzle 2. The chamber 6 may be at least partially tubular, cylindrical, elongate or conical in shape.

In the embodiment shown, the aerosol 3 is introduced into the chamber 6 in the direction of spraying of the discharge nozzle 2, along a longitudinal extent of the inhaler 1 or in the direction of flow in the region of the discharge nozzle 2 or axially in the direction of the longitudinal axis L of the inhaler 1.

The chamber 6 and the dispensing device 7 may be formed separately or in several pieces, for example, by a connection in the region of the connecting line 8 indicated by dashed lines. In the embodiment shown, the chamber 6 is formed in one piece with the dispensing device 7, particularly an adapter for a body orifice, particularly the nose or a nostril 9. In this way, depressions or gaps to which impurities might adhere or where they might get in are avoided.

The chamber 6 is preferably at least substantially rigid in construction. However, the chamber 6 may theoretically also be of flexible and/or telescopic configuration, particularly in order to minimize the space taken up when not in use and/or for carrying. In the embodiment shown the chamber 6 is formed from a dimensionally stable, flexible material and merges fluidically without a gap into the dispensing device 7 to ensure continuous flow guidance. However, it is not impossible that the dispensing device 7 is connected to the chamber 6 by latching and/or clamping or by a bayonet connection, by screwing or the like. However, other design solutions are also possible here.

The dispensing device 7 preferably comprises or forms a soft end piece. The dispensing device 7 is preferably embodied as a nasal adapter for insertion into the nostrils 9 of a horse 5 or other animal, particularly a large animal, as shown in schematic cross-section in FIG. 1. In particular, the inhaler 1 or the chamber 6 or the dispensing device 7 is embodied so that the aerosol 3 can be introduced preferably into the left nostril 9 of the horse 5. The chamber 6 and/or the dispensing device 7 may be transparent or made of transparent plastics. This makes it possible to monitor the aerosol formation.

The dispensing device 7 preferably comprises an outlet 10 which engages or can be introduced into the nostrils 9 or a nasal passage 11 of the horse 5 or some other body orifice and can connect the chamber 6 or the dispensing device 7 fluidically with the body orifice. Particularly preferably, the dispensing device 7 is configured such that the outlet 10 always opens into the correct nasal passage 11 and not in a blind passage.

The chamber 6 preferably has a volume of more than 0.05 l, particularly more than 0.1 l, particularly preferably about 0.1 to 0.4 l. Preferably, the size of the chamber 6 is adapted to the inhaler 1 such that the aerosol 3 formed on actuation of the inhaler 1 can be at least substantially completely received by the chamber 6, particularly without the aerosol 3 or the nebulized medicament preparation 4 being precipitated or deposited on the inner wall of the chamber to any great extent.

FIGS. 2 and 3 show a detail of the proposed inhaler 1 in the relaxed state and in the tensioned state.

The inhaler 1 is particularly embodied as a soft-mist inhaler as described at the beginning. This is described in more detail hereinafter with reference to the details in FIGS. 2 and 3.

The inhaler 1 preferably comprises a container 12 with the medicament preparation 4. The medicament preparation 4 is preferably arranged, or adapted to be arranged, inside the container 12 in a pouch 13.

Preferably, the container 12 is fixedly, non-detachably or non-removably integrated in the inhaler 1, particularly in such a way that the container 12 cannot be removed, or at least cannot be removed non-destructively or without causing damage. It is thus preferable for the inhaler to be a single-use or disposable product. However, other embodiments are also possible.

The inhaler 1 may preferably comprise a device for forced ventilation of the container 12. In particular, when it is tensioned or actuated for the first time, the base of the container 12 may be pierced or opened. Alternatively or additionally, it is opened when the container 12 is placed or inserted into the inhaler 1, or as a result of this action. In particular, an axially acting spring 15 arranged in a housing 14 of the inhaler 1 or a carrier of the inhaler 1 for the container 12 or some other opening or perforating element comes to abut on the base 16 of the container, piercing the container 12 or an, in particular, gastight seal on the base by means of a piercing element 17 when brought into contact for the first time, for ventilation purposes.

The forced ventilation device is thus formed here by the piercing element 17 which is held or formed by the spring 15. The piercing element 17 may also be formed without a spring 15. However, other design solutions are also possible.

It should be noted that during the piercing or venting, only the outer shell of the container 12 is opened. The pouch 13 preferably remains undamaged during the forced ventilation. As the medicament preparation 4 is taken from the pouch 13 the pouch 13 can collapse and to equalize the pressure ambient air 18 can flow through the venting or piercing opening in the container 12.

Before the inhaler 1 is used for the first time, the inhaler 1 is preferably tensioned and released several times. This so-called priming causes any air present in a delivery tube 19 and in a pressure generator 20 right up to discharge nozzle 2 to be expelled from the medicament preparation 4. The inhaler 1 is then ready for the inhalation.

The quantity of medicament preparation 4 delivered per stroke or actuation process is preferably about 10 μl to 50 μl, particularly about 10 μl to 20 μl, most preferably about 15 μl.

A tensioning element 21, preferably a drive spring, is preferably installed in a pretensioned state in order to achieve a high delivery pressure. In the proposed inhaler 1 the pressurizing and conveying of the medicament preparation 4 during the nebulization process are preferably carried out exclusively by means of energy stored in the tensioning element 21, particularly spring force. The inhaler 1 is thus also preferably configured so that the aerosol formulation is independent of a tensioning process, even if prior tensioning may be a prerequisite for the aerosol formation. Preferably, the inhaler 1 is configured so that the aerosol formation, particularly the dose, the discharge rate and/or the discharge speed, are independent of the tensioning process or are not influenced by the tensioning process. This ensures reliable dosing.

The inhaler 1 is preferably embodied so that the medicament preparation 4 in the pressure generator 20 in a pressure chamber 22 achieves a pressure of 5 MPa to 60 MPa, particularly 10 MPa to 50 MPa on discharge. Particularly preferably, during the delivery or nebulization of the medicament preparation 4, a pressure of about 50 MPa to 60 MPa, particularly about 10 MPa to 30 MPa is reached at the discharge nozzle 2 or its nozzle openings. The medicament preparation 4 is then converted into the aerosol 3, the droplets of which have an aerodynamic diameter of up to 20 μm, preferably about 3 μm to 10 μm. The nebulizing action or the nebulizing effect is achieved or further assisted by means of preferably intersecting sprays expelled from the discharge nozzle 2.

The inhaler 1 is preferably embodied such that the aerosol 3 is dispensed at low speed, particularly at a speed of less than 2 m/s, particularly about 1.6 m/s or less (measured in each case at a distance of 10 cm from the discharge nozzle 2). The inhaler 1 is thus preferably embodied as an SMI. The low dispensing speed can be achieved or assisted, in particular, by intersecting sprays of the medicament preparation 4 dispensed from the discharge nozzle 2, and/or by a suitable choice of spring force for the tensioning element 21.

Particularly preferably, the inhaler 1 is configured such that the aerosol production lasts for more than 0.7 s, preferably substantially 1 s or longer, particularly more than 1.5 s. The time taken to nebulize a dose or for actuation of the inhaler 1 is thus preferably more than 0.75 s, particularly about 1 s or more.

The inhaler 1 further comprises a delivery device or a pressure generator 20 for delivering and nebulizing the medicament preparation 4, particularly in a predetermined, optionally selectable metered quantity, or for nebulizing metered amounts or amounts capable of being metered. The inhaler 1 is thus able to dispense the medicament preparation 4 in a plurality of defined doses, preferably as an aerosol 3. Preferably, one dose can be dispensed by one actuation of the inhaler 1.

The inhaler 1 or pressure generator 20 is particularly configured such that the delivery, pressure generation and/or nebulization is carried out without the use of propellant gas, mechanically and/or by the energy or force of an energy storage device, particularly a spring device, particularly preferably by spring force, and in the embodiment shown by a drive spring, helical spring or other tensioning element 21. However, other design solutions are also possible. It is preferable if the nebulization is carried out independently of any manual operation, particularly independently of the speed of actuation of the inhaler 1 or driven exclusively by the energy stored in the tensioning element 21.

The inhaler 1 or pressure generator 20 comprises a pumping device 24, preferably with a holder 25 for the container 12 and/or with a delivery element, preferably with the delivery tube 19 embodied as a capillary, with an optional valve, particularly a non-return valve 23. The pumping device 24 is thus preferably an assembly of the pressure generator 20 which comprises the delivery tube 19 and means for moving it.

The pressure generator 20 may further comprise the pressure chamber 22 and/or the discharge nozzle 2, particularly in a transitional region to the chamber 6.

The pumping device 24 may be movable or drivable, particularly by the tensioning element 21. It is preferable if the pumping device 24 can be driven solely by the tensioning element 21 in order to discharge the medicament preparation 4.

The container 12 is fixed in the inhaler 1 by means of the holder 25, particularly by a clamping or latching action, so that the delivery tube 19 dips into the container 12. The holder 25 may be configured such that the container 12 can be non-detachably fixed, preferably latched.

The inhaler 1 comprises an actuating lever 26 for preferably axial tensioning of the tensioning element 21. During the tensioning of the tensioning element 21 the pumping device 24 is preferably moved with the container 12, downwards in the embodiment shown, and the medicament preparation 4—or to be more accurate the next dose—is aspirated out of the container 12 into the pressure chamber 22 of the pressure generator 20 by means of the non-return valve 23.

During the subsequent relaxation of the tensioning element 21, particularly after operation of an initiating device 27, the medicament preparation 4 is put under pressure in the pressure chamber 22. For this purpose, the pumping device 24 or the delivery tube 19 can be moved back up, with the non-return valve 23 now closed, by relaxation of the tensioning element 21 and can now act as a pressure ram. Preferably, for this purpose, the pumping device 24 with the delivery tube 19 can be moved in a linear or axial manner, particularly exclusively, by the tensioning element 21. This pressure forces the medicament preparation 4 out through the discharge nozzle 2, where it is converted into the preferably respirable aerosol 3, as shown in FIGS. 1 and 2.

FIG. 4 shows a proposed container 12 according to a first embodiment in cross-section.

The container 12 preferably forms a reservoir for the medicament preparation 4 which is to be nebulized. Preferably, the container 12 contains a sufficient quantity of medicament preparation 4 or active substance for a plurality of doses of the medicament preparation 4, i.e., to enable a plurality of nebulization or applications. A typical container 12 holds a volume of about 2 to 10 ml.

It is preferable if the container 12 has a volume which is less than 50 ml, preferably less than 30 ml, particularly less than 20 ml. This provides a compact construction for the inhaler 1 and ensures that the medicament preparation 4 will be used up before its expiry date.

The container 12 is preferably substantially cylindrical or cartridge-shaped. The container 12 is preferably of rigid construction, while the medicament preparation 4 is held or adapted to be held in the collapsible pouch 13 in the container 12. The container 12 is preferably connectable to a dispensing device, particularly the inhaler 1.

It is particularly preferable if the container 12 has a rigid outer sleeve 28. The sleeve 28 preferably comprises aluminum or is at least partially, at least substantially or completely made of aluminum or another metal. The sleeve 28 preferably has an (average) wall thickness of more than 50 µm, preferably more than 70 µm. The sleeve 28 may alternatively or additionally also contain plastics, preferably a thermoplastic, particularly polybutylene terephthalate (PBT), or be made from said plastics.

The container 12 preferably comprises the collapsible pouch 13 which is configured to hold the medicament preparation 4 or contains the medicament preparation 4.

The container 12 or the sleeve 28 is preferably closed off in airtight or gastight manner by a cover 29, particularly a sealing film, while for operating the device the delivery tube 19 can pierce the cover 29 to provide a fluidic connection on the inside of the pouch 13 for removal of the medicament preparation 4.

The sleeve 28 preferably surrounds or embraces an inner space 30 of the container 12. The inner space 30 preferably comprises the inner pouch 29 or is configured in some other way for holding, dispensing and/or storing the preferably liquid medicament preparation 4.

The sleeve 28 is preferably closed off by a stopper 31. The stopper 31 preferably forms a tightly sealing and/or centered guide for a removal connector or the delivery tube 19. The stopper 31 is preferably connected to the sleeve 28 in sealed, particularly airtight manner, and/or non-detachably connected, particularly fitted.

The container 12 preferably comprises a neck region 32 in which the sleeve 28 is closed off by the stopper 31. In the neck region 32 the container 12 is preferably configured to be held on or in the inhaler 1. In particular, the container 12 comprises in the neck region 32 one or more, particularly annular, grooves, undercuts, projections, indentations, shoulders or other interlocking means for preferably securing the container 12 on or in the inhaler 1 by locking.

When medicament preparation 4 is taken from the container 12, particularly from the pouch 13, the volume of the pouch 13 decreases and a negative pressure is formed in the inner space 30 of the container 12. To equalize the negative pressure thus formed, the container 12 preferably has a venting device 33.

The venting device 33 is preferably configured to allow ambient air 18 to penetrate into the inner space 30 and thus allow equalization of pressure.

The present invention relates particularly to the venting device 33 of the container 12, which particularly preferably comprises, or is formed by, a multi-layered wall structure 34 delimiting the inner space 30.

The wall structure 34 preferably comprises a first layer 35 in which a first through-opening 36 is provided. It is preferable if the, in particular hydraulic, diameter of the first through-opening 36 is less than 40 µm. This advantageously minimizes the loss of constituents of the medicament preparation 4 through the venting device 33.

Alternatively or additionally, it is particularly preferred if the wall structure 34 has a second layer 37 with a second through-opening 38. In the embodiment shown, the second layer 37 is formed by the bottom wall of the sleeve 28 or a wall that forms the container 12 or encloses the inner space 30.

It is also preferable if the wall structure 34 comprises a third layer 39, particularly a sealing layer, sealing film or a third layer 39 configured in some other manner for sealing the inner space 30 or the through-openings 36, 38, particularly in airtight manner.

A layer in the sense of the present invention is preferably a flat and/or one-piece structure. In particular, the first layer 35 and/or the second layer 37 and/or the third layer 39 is formed in one piece.

The layers 35, 37, 39 may be coated, particularly with adhesive, and/or may be adhesively bonded to one another. The layers 35, 37, 39 are preferably directly in material contact with one another and/or are joined to one another solely by an adhesive bond, preferably rigidly, fixedly and/or over their surface.

The first layer 35 and the second layer 37 are preferably fixedly or non-detachably connected, or connectable, to one another. A non-detachable connection is preferably one which allows separation of the first layer 35 from the second layer 37 only by damaging or destroying the first layer 35 and/or the second layer 37. Alternatively or in addition to one or more of the adhesive bonds, one or more of the layers 35, 37, 39 may also be welded together or welded onto one another, particularly by ultrasonic welding, particularly preferably if at least one of the welded layers contains plastics or is formed of plastics, particularly a thermoplastic, particularly PBT.

Figure 4:
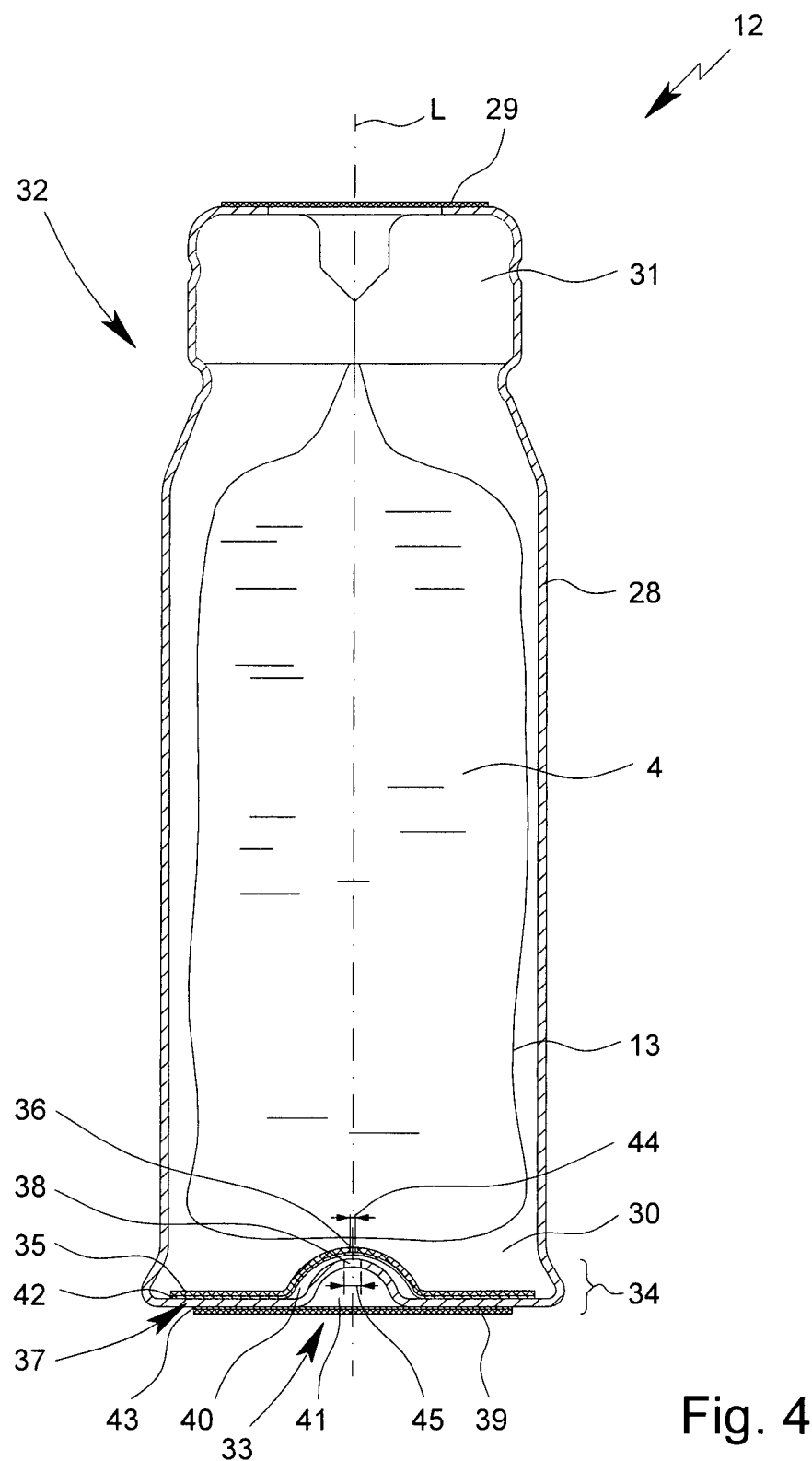
FIG. 4 is a cross-section of a proposed container with a proposed wall structure according to a first embodiment.
Figure 5:
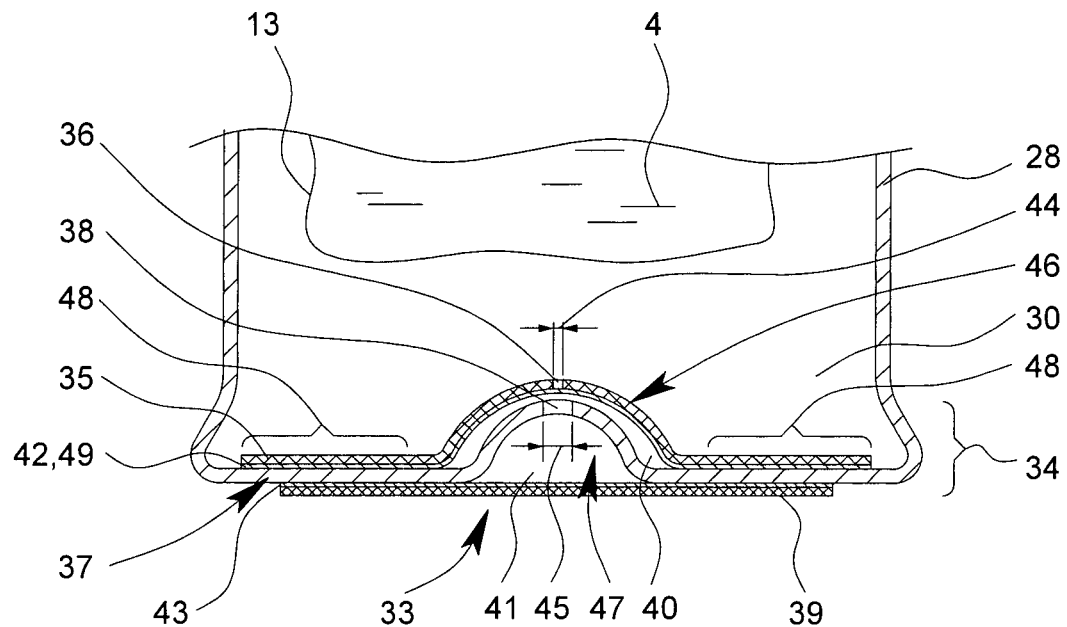
FIG. 5 is a detail of the embodiment according to FIG. 4 in the region of the wall structure.

FIG. 5 shows a schematic detail of the (forced) venting device 33 or the wall structure 34 of the container 12 according to the embodiment from FIG. 4.

In the embodiment according to FIG. 5 the first layer 35 comprises only a single, namely the first, through-opening 36, which preferably has a (hydraulic) diameter 44 of less than 40 µm, preferably less than 30µ, and/or greater than 10 µm, preferably greater than 15 µm, particularly at least substantially 25 µm.

In the embodiment according to FIG. 5 the first layer 35 is formed separately from the second layer 37. The second layer 37 is embodied as part of the sleeve 28.

The first through-opening 36 has a (hydraulic) diameter 44, which is many times smaller than the (hydraulic) diameter 45 of the second through-opening 38 of the second layer 37, preferably by a factor of more than four, six or ten.

In the present embodiment, the first layer 35 is provided or arranged with the first through-opening 36 additionally congruent with the second layer 37 and/or the second through-opening 38. This ensures that the first through-opening 36 and the second through-opening 38 are connected fluidically behind one another. As a result, the first layer 35 reduces the minimum diameter of the fluid connection formed by the second through-opening 38, so that the effects described can be obtained.

The first layer 35 is preferably sealingly connected to the second layer 37 over a large area, particularly preferably materially connected. In particular, more than 20%, preferably more than 30%, particularly more than 40% of the surface of the first layer 35 facing the second layer 37 is connected to or in contact with the second layer 37, particularly materially or adhesively bonded. In this way it is possible to achieve a particularly good, stable, long-lasting and sealed, particularly diffusion-proof, connection of the first layer 35 with the second layer 37. A leak-tight connection of this kind is advantageous so that the intended small (hydraulic) diameter 44 of the first through-opening 36 is not affected or damaged by leaks or diffusion between the first layer 35 and the second layer 37.

The first layer 35 is particularly preferably spaced from the second layer 37 at least in the region of the first through-opening 36 or the second through-opening 38. This prevents the first through-opening 36 with the small (hydraulic) diameter 44 from being adversely affected, particularly changed in its effective cross-section by deformation or by the ingress of particles.

Preferably, an interstice 40 is formed between the first layer 35 and the second layer 37. Alternatively or additionally, a cavity 41 is formed between the second layer 37 and the third layer 39.

The interstice 40 or the cavity 41 may have a volume which is greater than 0.2 μl, preferably greater than 0.5 μl, particularly greater than 1 μl and/or less than 10 μl, preferably less than 6 μl, particularly less than 4 μl. In this way, a sufficient safety gap can be achieved in respect of the interstice 40. With regard to the cavity 41, in the embodiment according to FIG. 5, perforation or piercing of the third layer 39 is possible without affecting the second through-opening 38 or even the first through-opening 36.

The spacing between the first layer 35 in the region of the first through-opening 36 and the second layer 37 and/or the third layer 39 is preferably more than 20 μm, preferably more than 50 μm, particularly more than 100 μm or 200 μm, and/or less than 3 mm, preferably less than 2 mm, particularly less than 1 mm.

Preferably, the venting device 33 or the wall structure 34 comprises between the first layer 35 and the second layer 37 a first material connection, particularly a sealing or adhesive bond 42. Alternatively or additionally, the forced venting 33 or the wall structure 34 preferably comprises a material connection, particularly a second adhesive bond 43, between the second layer 37 and the third layer 39.

The first adhesive bond 42 or the second adhesive bond 43 may be configured as a layer, particularly as a layer of hot melt adhesive, a sealing layer or the like, and/or may be configured with a layer thickness of more than 10 μm, preferably more than 15 μm and/or less than 50 μm, particularly less than 40 μm, particularly preferably about 25 μm. It has been found, surprisingly, that a layer thickness of this order can ensure a good bond with at the same time a low diffusion rate through the adhesive bond 42, 43.

Preferably, the first layer 35 is configured to be (heat-) sealed to the second layer 37. Alternatively or additionally, the first layer 35 may also be connected to the second layer 37 by welding, ultrasonic welding, soldering, clamping or by other means, preferably to form a leak-tight seal.

The wall structure 34 according to FIG. 5 is particularly advantageous owing to the fact that the first layer 35 is arranged inside the sleeve 28. As a result the first through-opening 36 is advantageously protected from external influences, particularly by or by means of the second layer 37.

The third layer 39 is preferably configured to be mechanically removed or destroyed. In particular, the third layer 39 is embodied as a film, plastics film, sealing film, composite film, thin aluminum foil or a combination or the like, which can be pierced, pulled off or otherwise opened. In this way, the fluidic connection between the inner space 30 and the environment formed by the first through-opening 36 and the second through-opening 38 can be opened up.

The third layer 39 is preferably arranged outside the sleeve 28. This allows easy access to the third layer 39 and enables the venting device 33 to be opened particularly easily and effectively by external action.

The first layer 35 and/or the second layer 37 preferably comprise(s) a convexity or indentation 46, 47. In this way the cavity 41 may be formed, allowing or favoring the piercing or puncturing of the third layer 39.

Particularly preferably, the convexity or indentation 46 of the first layer 35 is formed to correspond to the convexity or indentation 47 of the second layer 37. In particular, the first layer 35 is arranged and configured so that the convexity or indentation 47 of the second layer 37 lies in the convexity or indentation 46 of the first layer 35.

The convexities or indentations 46, 47 of the second layer 37 and first layer 35 are thus preferably at least substantially oriented with one another or arranged inside one another. For this reason the convexity or indentation 46 of the first layer 35 may have a larger diameter than the convexity or indentation 47 of the second layer 37 or vice versa. The diameters of the convexities or indentations 46, 47 thus differ, preferably at least such that the outer diameter of the innermost of the indentations or convexities 46, 47 is less than or equal to the inner diameter of the outermost of the indentations or convexities 46, 47.

The convexities or indentations 46, 47 can preferably be arranged one inside the other, can be fitted into one another or arranged to correspond to one another so as to be spaced apart when the layers 35, 37 abut on one another in the area surrounding the convexities or indentations 46, 47.

It is preferable if the first through-opening 36 is provided in the center of the convexity or indentation 46 of the first layer 35 and/or the second through-opening 38 is provided in the center of the convexity or indentation 47 of the second layer 37. However, other solutions are also possible.

It is preferable if the first through-opening 36 is aligned with the second through-opening 38 and the first through-opening 36 and the second through-opening 38 are both provided in the center of the convexity or indentation 46, 47 of the respective first layer 35 or second layer 37.

It is particularly preferable if the first layer 35 is of planar configuration, particularly with a layer thickness which is less than 100 μm, preferably less than 70 particularly less than 50 μm, at least in an area surrounding the first through-opening 36.

It is preferable if the first layer 35 is formed without interruptions, apart from the first through-opening 36. This prevents diffusion taking place through the first layer 35, which could detract from the effect of the small diameter of the first through-opening 36. In particular, the first layer 35 is thus an aluminum foil which comprises a single through-opening, namely the first through-opening 36, particularly preferably in a convex or indented region which may be produced particularly by embossing or thermoforming and/or deep drawing.

The first through-opening 36 is preferably produced by laser drilling. This allows a particularly precise and uniform shape to be obtained for the through-opening 36 or its diameter 44.

In FIGS. 4 and 5 the material connections, particularly adhesive layers or adhesive bonds 42, 43, are provided at least substantially over the entire surface of one of the flat sides of the first layer 35 and/or the second layer 37. However, it is alternatively or additionally possible and preferable for this to be interrupted, absent, cut away or recessed in the region of the first through-opening 36 and/or the second through-opening 38. In particular, the adhesive or the respective adhesive bond 42, 43 is provided only in the respective connecting portion 48. In particular, no adhesive coating or adhesive bond 42, 43 is provided in the region of the convexity or indentation 46, 47.

Figure 6:
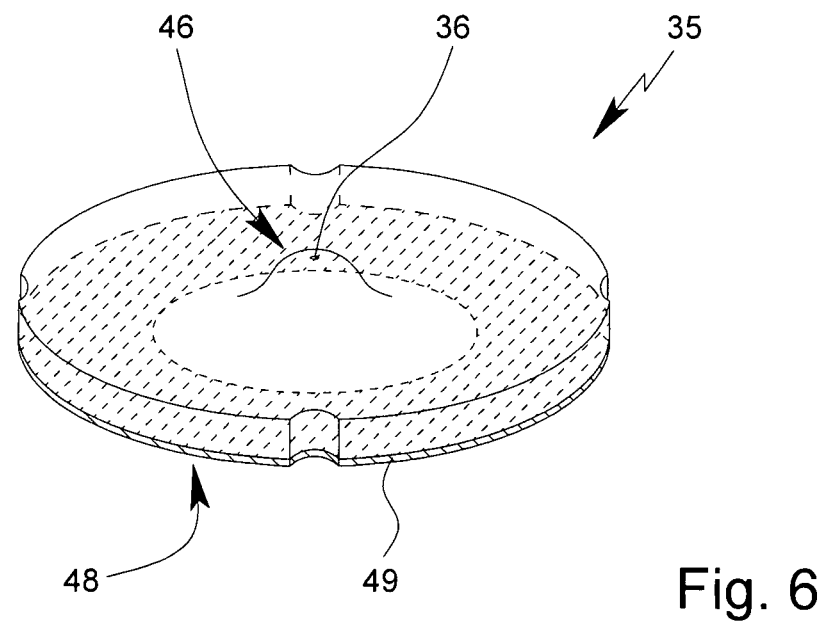
FIG. 6 is a schematic detailed view of the first layer.

FIG. 6 shows a first layer 35 in the uninstalled state.

The first layer 35 is preferably formed as a flat surface or film. In the embodiment shown, the first layer 35 is formed at least substantially of metal, particularly aluminum. Alternatively or additionally, the first layer 35 may also comprise plastics, preferably a thermoplastic, particularly polybutylene terephthalate (PBT), or may be formed at least substantially or completely therefrom.

The first layer 35 is preferably formed in one piece. The first layer 35 may comprise an adhesive layer, an adhesive coating or the like or be connected thereto, particularly by material bonding.

The first layer 35 is preferably at least substantially round and/or shaped to fit the base of the container 12 or the sleeve 28. The first layer 35 may have recesses on its edge which preferably correspond to the shape or to obstacles on or in an inner side wall of the container 12 or the sleeve 28. This simplifies the insertion of the first layer 35.

The first layer 35 is preferably configured to cover the inner base of the sleeve 28 or of the container 12 by more than 50%, preferably more than 65%, particularly more than 80% or at least substantially completely. It has been found that this improves a leak-tight bonding of the first layer 35 to the second layer 37.

The first layer 35 preferably has an area which is greater than 0.5 cm$^2$, particularly greater than 1 cm$^2$, and/or less than 4 cm$^2$, particularly less than 3 cm$^2$.

The convexity or indentation 46 of the first layer 35 preferably takes up less than 30%, particularly less than 20% of the entire area of the first layer 35.

The convexity or indentation 46 of the first layer 35 is preferably provided in the center of or at least substantially at the center of gravity of the area formed by the first layer 35.

The first through-opening 36 is provided in the convexity or indentation 46 of the first layer 35 and/or in the center of or at least substantially at the center of gravity of the first layer 35.

The first layer 35 is preferably formed to be at least substantially symmetrical, particularly mirror-symmetrical and/or rotationally symmetrical, to the first through-opening 36. However, other solutions are also theoretically possible.

In particular, the first through-opening 36 may theoretically not be in the center and/or the first layer 35 may be of asymmetrical construction, for example, if this is necessary to ensure that the first layer 35 corresponds to the structure of the surface of the second layer 37 or the sleeves 28 or if the second layer 37 is asymmetrical.

The first layer 35 preferably comprises, on the side remote from the convexity or indentation 46, in particular, a ring-shaped connecting portion 48 for connecting to the second layer 37 or to the sleeve 28 or another wall of the container 12.

Particularly preferably, the first layer 35 comprises, in the connecting portion 48, a coating 49, particularly for the leak-tight application of the first layer 35 by material bonding. Preferably, the coating 49 is provided only in the connecting portion 48.

The connecting portion 48 is preferably arranged at the edges of the first layer 35 and/or takes up less than 70%, preferably less than 50%, of the surface of the first layer 35 on the side that carries the coating 49. The coating 49 is preferably provided only on one flat side of the first layer 35, particularly on the flat side of the first layer 35 which is remote from the convexity or the top of the dome or that which faces the indentation 46 in the first layer 35.

In a method for producing a proposed container 12 which can also be implemented independently, the first layer 35 is sealed into the sleeve 28 or other container blank.

It is preferably provided that the first layer 35 with the first through-opening 36 forms an inlay which can be arranged, or has been arranged, inside the sleeve 28 or inside the container 12 or in the inner space 30, particularly so as to form a continuous fluidic connection between the inner space 30, the first through-opening 36 and the second through-opening 38, preferably as far as the third layer 39.

Preferably, after insertion, the first layer 35 is connected to the second layer 37 in the connecting portion 48 and/or by means of the coating 49. The coating 49 may alternatively or additionally also be provided on the second layer 37.

The coating 49 preferably forms the materially connected or first adhesive bond 42 by sealing, heating, drying, contacting, or the like. For producing a leak-tight bond between the first layer 35 and the second layer 37, the coating is preferably fused on. However, it is also possible for the first layer 35 to be connected to the second layer 37, the sleeve 28 and/or the container 12 by material bonding, interlocking engagement and/or sealing in some other way.

It is particularly preferable if the first layer 35 is provided with the first through-opening 36 and/or convexity or indentation 46 as an inlay or even before it is installed. For this purpose, the first layer 35 may be stamped out of a film material and/or the convexity or indentation 46 may be introduced, particularly by embossing, vacuum-forming and/or thermoforming and/or deep drawing, and/or the first through-opening 36 may be drilled, particularly by laser drilling.

The first layer 35 is preferably applied as a lacquer. In particular, the first layer is applied to a flat side facing the convexity or the top of the dome thereof or painted on with nitrocellulose, preferably with a basis weight of more than 0.2 g/m$^2$, preferably more than 0.5 g/m$^2$, particularly more than 0.8 g/m$^2$, and/or less than 3 g/m$^2$, preferably less than 2 g/m$^2$, particularly less than 1.5 g/m$^2$ or about 1 g/m$^2$. The lacquer coating is preferably also drilled or preferably also comprises the first through-opening 36.

The first layer 35 comprises, at least in the region of the first through-opening 36 and/or on average, a material thickness which is less than 100 µm, preferably less than 70 µm, particularly less than 55 µm, and/or more than 20 µm, preferably more than 30 µm, particularly more than 35 µm, particularly preferably about 45 µm.

The first layer 35 is preferably a thermo-weldable aluminum composite film. The first layer 35 is preferably cut from endless strip or endless material, particularly by stamping. This has proved particularly efficient.

The first layer 35 is preferably sealed into the sleeve 28 by heat-sealing. During the heat-sealing, a bond is preferably formed by the combination of pressure and a supply of heat. The first layer 35 is thus preferably pressed onto the inner sleeve base and at the same time heated, preferably to above 350° Kelvin, particularly above 380°, 400° or 430° and/or below 500° Kelvin. For this purpose, the first layer 35 is preferably held against a sealing punch, particularly by suction, and applied to the inner base of the sleeve 28 by inserting the sealing punch into the sleeve 28. By heating, the first layer 35 can then be bonded to the sleeve 28 or the second layer 37. Preferably, a sealing means, an adhesive or the like previously introduced into the sleeve 28 or applied to the first layer 35 and/or the second layer 37 is melted so as to produce an air-tight joint.

It is preferable if the first through-opening 36 is drilled before the insertion or sealing. However, it is also possible for the first through-opening 36 only to be made after the installation or sealing of the first layer 35.

Different embodiments of the proposed venting device 33 or the proposed wall structure 34 will be described in more detail hereinafter with reference to the additional FIGS. 7 to 11, in which the same reference numerals are used for identical or similar parts and the same or similar properties are present and/or the same or similar advantages are obtained, even though the relevant description is not repeated. In the following description, only essential differences are discussed and the explanations provided hereinbefore are of a corresponding supplementary nature wherever this is technically possible.

Figure 7:
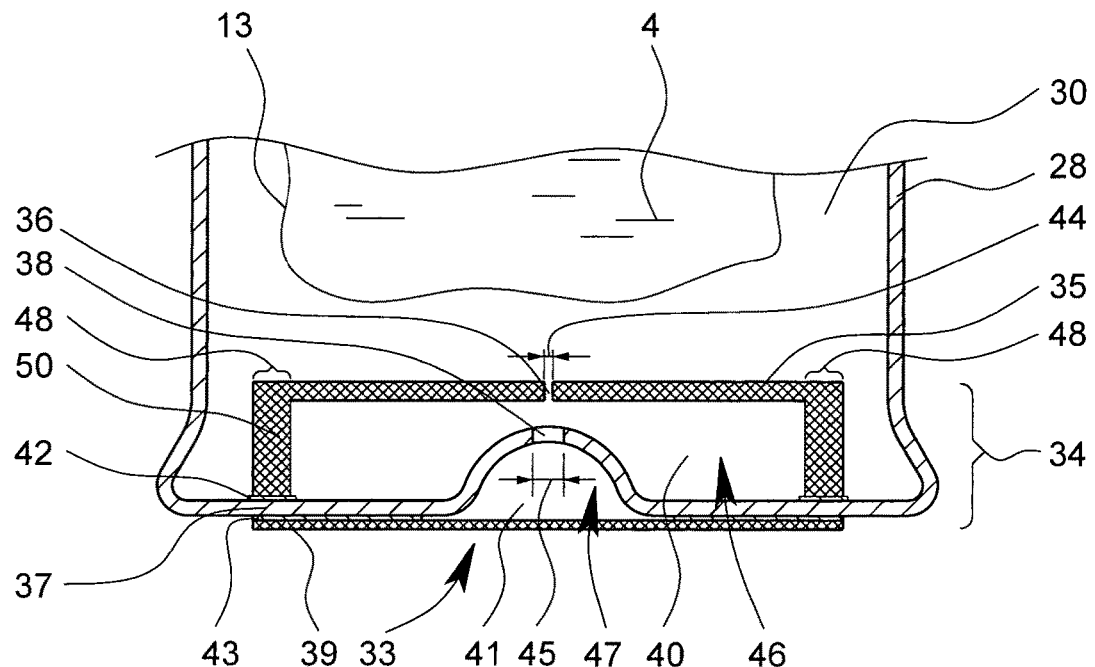
FIG. 7 is a detail of the proposed container in the region of the wall structure according to a second embodiment.

FIG. 7 shows a detail of a proposed container 12 with a proposed wall structure 34 according to a second embodiment, in which the first layer 35 is configured differently from the first layer 35 in the first embodiment. In the second embodiment the first layer 35 is arranged in the manner of a housing, a cover or a box above the portion of the second layer 37 with the second through-opening 38.

In particular, the first layer 35 is of pot-shaped or cylindrical configuration, the first through-opening 36 being particularly preferably provided in the center, in the center of gravity of a cover surface and/or on an axis of symmetry or along an axis of symmetry of the first layer 35.

The first layer 35 comprises one or more side walls 50 which are arranged at least substantially transversely or perpendicularly to and/or at the end face of the second layer 37 or are connected to the latter.

Figure 8:
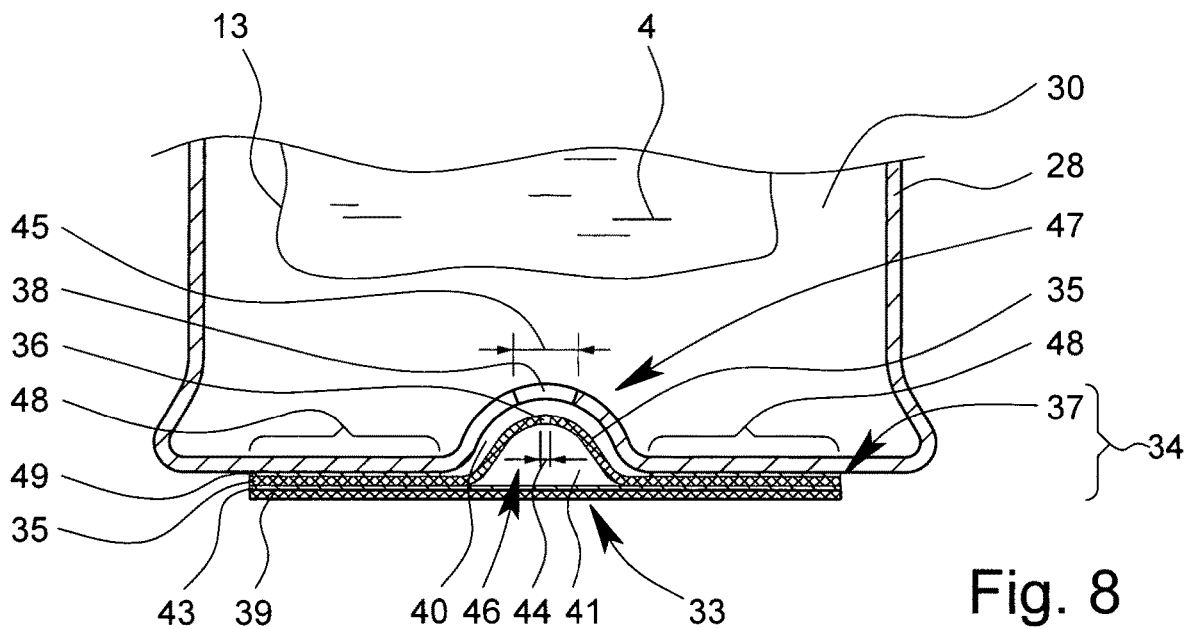
FIG. 8 is a detail of the proposed container in the region of the wall structure according to a third embodiment.

FIG. 8 shows a detail of a proposed container 12 with a proposed wall structure 34 according to a third embodiment.

In this embodiment, the first layer 35 is provided on the side of the second layer 37 remote from the inner space 30. This facilitates the subsequent provision of the first layer 35 or the first through-opening 36.

Preferably, the convexity or indentation 46 of the first layer 35 is configured such that it can be inserted or arranged in the convexity or indentation 47 of the second layer 37. In particular, the convexity or indentation 46 of the first layer 35 has a diameter which is less than the diameter of the convexity or indentation 47 of the second layer 37.

The coating 49 is preferably provided on the side facing the convexity of the first layer 35 or the side remote from the indentation 46 of the first layer 35, particularly at the edges. This makes it possible for the convexity or indentation 46 of the first layer 35, particularly in the connecting portion 48, to be sealingly connected to the second layer 37, particularly by material bonding.

Figure 9:
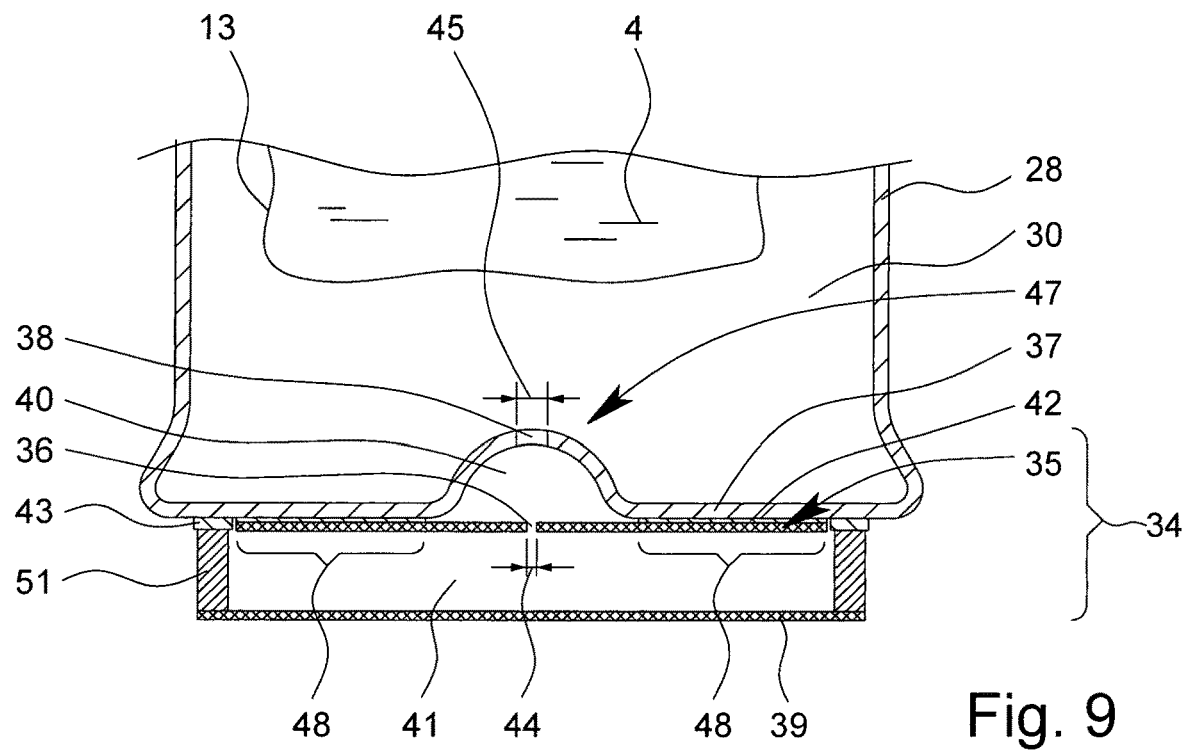
FIG. 9 is a detail of the proposed container in the region of the wall structure according to a fourth embodiment.

FIG. 9 shows a detail of a proposed container 12 with a proposed wall structure 34 according to a third embodiment.

In the third embodiment the first layer 35 is of planar configuration at least substantially and/or in the region of the first through-opening 36. Thus, no convexity or indentation 46 is provided.

The first layer 35 is arranged between the second layer 37 and the third layer 39 in the fourth and also in the third embodiment. In the fourth embodiment the third layer 39 is formed in the manner of a housing, a box and particularly a cylinder or cylindrical section.

In the embodiment shown, the third layer 39 is preferably directly connected to the second layer 37, particularly by its end faces or one or more side walls 51, and/or receives the first layer 35. Alternatively or additionally the third layer 39 may, however, also be correspondingly connected to the first layer 35 (not shown).

Figure 10:
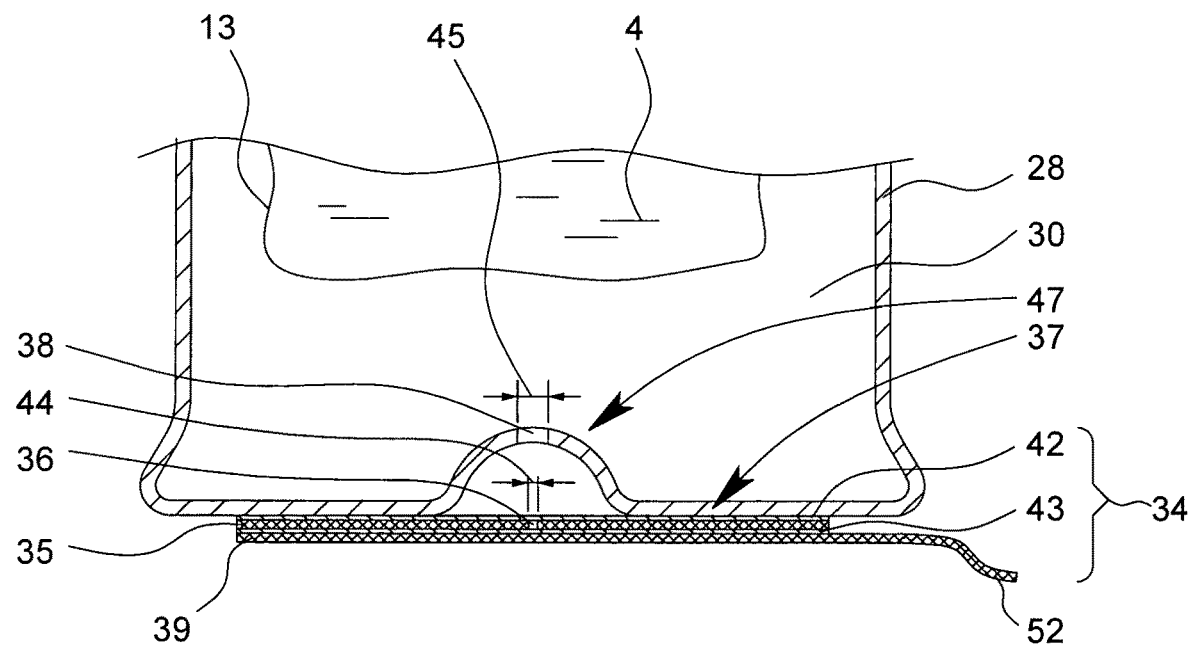
FIG. 10 is a detail of the proposed container in the region of the wall structure according to a fifth embodiment.

FIG. 10 shows a detail of a proposed container 12 with a proposed wall structure 34 according to a fifth embodiment. The first layer 35 is arranged here between the second layer 37 and the third layer 39.

The third layer 39 preferably abuts on the first layer 35 and/or second layer 37 directly or separated only by an adhesive layer.

In the fifth embodiment, unlike in the previous embodiments, the third layer 39 is configured to be manually removable. For this purpose the third layer 39 preferably comprises a tab 52 or a tab-like projection by means of which the third layer 39 can be pulled away from the first layer 35 and/or the second layer 37.

Figure 11:
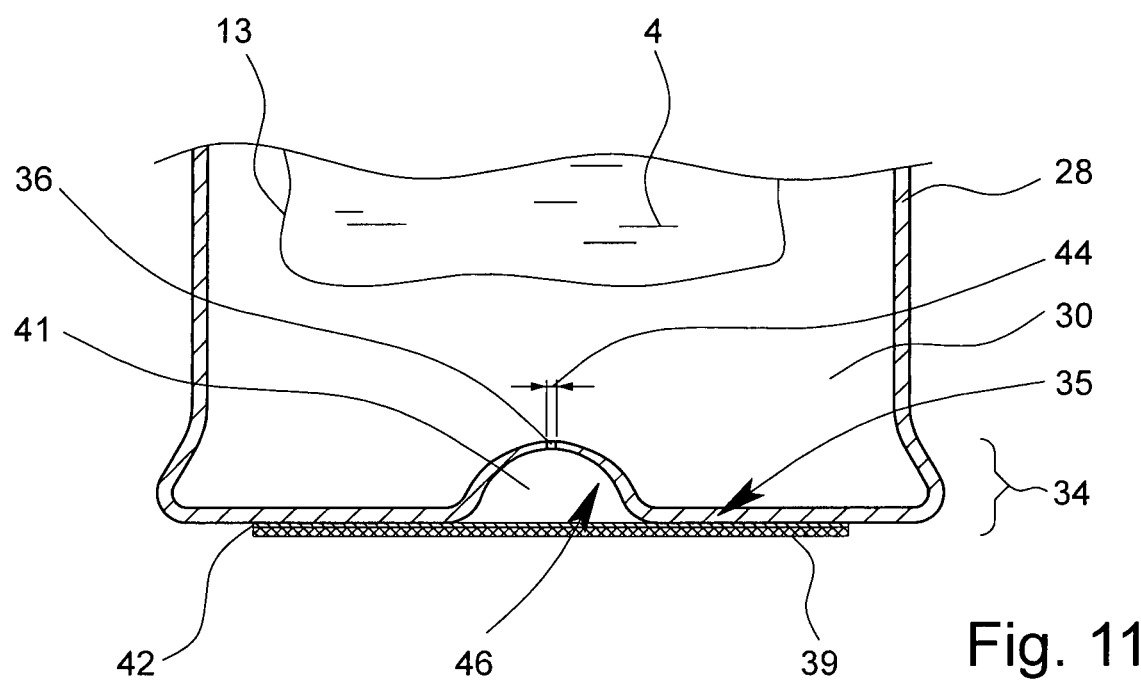
FIG. 11 is a detail of the proposed container in the region of the wall structure according to a sixth embodiment.

FIG. 11 shows a detail of a proposed container 12 with a proposed wall structure 34 according to a sixth embodiment.

In the sixth embodiment, there is no second layer 37. Instead, the first layer 35 is preferably formed by the sleeve 28, the container 12 or a wall forming the container 12.

Preferably, the material thickness of the first layer 35, at least in the immediate vicinity of the first through-opening 36, is reduced to preferably less than 200 μm, particularly to less than 150 μm or 100 μm. This permits or favors the introduction of a first through-opening 36 with corresponding diameters.

In another aspect of the present invention which can also be implemented independently, the proposed container 12, particularly with the inhaler 1, is used to produce the aerosol 3 with a medicament preparation 4 held in the container 12, particularly in the pouch 13.

In another aspect of the present invention which can also be implemented independently, the proposed container 12 and/or inhaler 1 is used for therapeutic purposes, particularly for holding, dispensing and/or storing a preferably liquid medicament preparation 4.

In another aspect of the present invention which can also be implemented independently, the proposed container 12 is used in an inhaler 1 or other device for dispensing particularly liquid medicament preparations 4, the third layer 39 being destroyed, perforated and/or removed as the container is inserted, or as a result of it being inserted, so that the medicament preparation 4 can be dispensed, particularly for therapeutic purposes.

The individual aspects of the various embodiments may be combined with one another in numerous ways. For example, the third layer 39 may be removable and/or spaced apart or pot-shaped in different embodiments.

What is claimed is:

1. Container for holding, dispensing and/or storing a medicament preparation, comprising:
   an inner space for the medicament preparation and
   a venting device with a partially multi-layered wall structure, the wall structure comprising an innermost first layer in which a first through-opening is provided that is in communication with said inner space, the first through-opening having a diameter of less than 40 μm as a means for reducing the escape of volatile constituents from the inner space and improving shelf life while ensuring adequate ventilation,
   wherein the wall structure further comprises a second layer and a third layer, wherein a second through-opening which is larger in size from the first through-opening is arranged in the second layer and the third layer is located on an outer side of the wall structure and covers or closes off the through-openings of the first and second layers.

2. Container according to claim 1, wherein the first through-opening and the second through-opening are fluidically connected to one another.

3. Container according to claim 1, wherein the first through-opening is at least one of tube-like, produced by laser drilling and the only through-opening in the first layer.

4. Container according to claim 1, wherein the diameter of the first through-opening is less 30 μm and more than 10 μm.

5. Container according to claim 1, wherein the first layer is substantially at least one of flat, film-shaped, plate-shaped, metallic and round.

6. Container according to claim 1, wherein the first layer comprises a convexity or indentation in which the first through-opening is arranged, the second layer also comprising a convexity or indentation, the convexity or indentation of the first layer corresponding to the convexity or indentation of the second layer.

7. Container according to claim 1, wherein the first layer is connected to the second layer by at least one of material bonding, and direct sealing, in an annular connecting portion of the first layer, the first through-opening and the second through-opening being provided in the region of an eyelet formed by the annular connecting portion.

8. Container according to claim 1, wherein the first through-opening and the second through-opening are arranged behind and in alignment with one another.

9. Container according to claim 1, wherein a clearance space is provided between the first layer and the second layer in a region of the first through-opening and the second through-opening.

10. Container according to claim 9, wherein the clearance space is greater than 20 μm.

11. Container according to claim 1, wherein the second layer is formed in one piece with a base of the container.

12. Container according to claim 1, wherein the second through-opening has a diameter which is greater than the diameter of the first through-opening.

13. Container according to claim 1, wherein the second through-opening has a diameter which is greater than 50 μm.

14. Container according to claim 1, wherein an interstice or cavity produced by thermoforming and/or deep drawing is formed between the second layer and the first layer or between the second layer and the third layer in a region of, or fluidically connected to, the first through-opening or the second through-opening.

15. Container according to claim 14, wherein the volume of the interstice or cavity is greater than 0.2 μl and less than 10 μl.

16. Container according to claim 1, where the medicament preparation is a liquid contained in a collapsible pouch within the interior space of the container.

17. Inhaler, comprising:
an inhaler body having a chamber therein,
a container disposed in said chamber and having an inner space for holding a liquid medicament preparation, and
a dispensing device for fluidically connecting the inner space of the container to a body orifice,
wherein the container comprises a venting device with an at least partially multi-layered wall structure, the wall structure comprising first layer in which a first through-opening is provided that is in communication with said inner space, the first through-opening being provided in the first portion and having a diameter of less than 40 μm as a means for reducing the escape of volatile constituents from the inner space and improving shelf life while ensuring adequate ventilation,
and
wherein the container comprises a second layer and a third layer, wherein a second through-opening which is different size from the first through-opening is arranged in the second layer and wherein the third layer or closes off the through-openings of the first and second layers, and
wherein a cutting element configured to cut through the third layer without adversely affecting the first layer is located in said chamber.

18. Method for producing a container for holding, dispensing and/or storing a liquid medicament preparation, comprising:
providing the container with an inner space for the medicament preparation and a venting device with an at least partially multi-layered wall structure defining a portion of the inner space, the wall structure comprising a first layer in which a first through-opening is provided, a second layer with a second through-opening which is different from the first through-opening and a third layer covering or closing off the wall structure,
comprising the further steps of:
providing an inlay with the first through-opening, the first through-opening being provided with a diameter of less than 40 μm as a means for reducing the escape of volatile constituents from the inner space and improving shelf life while ensuring adequate ventilation,
forming the first layer by placing the inlay in a sleeve that forms an outer wall of said container,
sealingly connecting the first layer to the sleeve in a region surrounding the first through-opening, and
placing the third layer on an outer side of the outer wall of said container.

19. Method according to claim 18, wherein the first through-opening is introduced into the first layer by at least one of: laser drilling, after the first layer has been thermoformed or deep drawn in the region of the through-opening, and before the first layer has been placed or sealed in the sleeve.

* * * * *